(12) United States Patent
Overmyer et al.

(10) Patent No.: US 11,666,404 B2
(45) Date of Patent: Jun. 6, 2023

(54) ARTICULATING INCLUDING ANTAGONISTIC CONTROLS FOR ARTICULATION AND CALIBRATION

(71) Applicant: Cilag GmbH International, Zug (CH)

(72) Inventors: Mark D. Overmyer, Cincinnati, OH (US); Benjamin Lawrence Bertram, Crestview, KY (US); Vincenzo Barbato, Cincinnati, OH (US); Kris Eren Kallenberger, Cincinnati, OH (US)

( * ) Notice: Subject to any disclaimer, the term of this patent is extended or adjusted under 35 U.S.C. 154(b) by 329 days.

(21) Appl. No.: 16/553,725

(22) Filed: Aug. 28, 2019

(65) Prior Publication Data

US 2021/0059777 A1 Mar. 4, 2021

(51) Int. Cl.
*A61B 34/00* (2016.01)
*A61B 34/30* (2016.01)
*A61B 17/00* (2006.01)
*A61B 17/072* (2006.01)

(52) U.S. Cl.
CPC .............. *A61B 34/71* (2016.02); *A61B 17/00* (2013.01); *A61B 34/30* (2016.02); *A61B 17/07207* (2013.01); *A61B 2017/00314* (2013.01); *A61B 2017/00327* (2013.01); *A61B 2017/00725* (2013.01); *A61B 2017/07285* (2013.01); *A61B 2034/715* (2016.02)

(58) Field of Classification Search
CPC combination set(s) only.
See application file for complete search history.

(56) References Cited

U.S. PATENT DOCUMENTS

| 8,876,820 | B2 * | 11/2014 | Hughett, Sr. ...... A61B 18/1445 606/41 |
| 2011/0319910 | A1 | 12/2011 | Roelle |
| 2012/0123441 | A1 | 5/2012 | Au |
| 2015/0374364 | A1 | 12/2015 | Gettinger |
| 2019/0125430 | A1 | 5/2019 | Shelton, IV |
| 2019/0183491 | A1 * | 6/2019 | Shelton, IV ... A61B 17/320016 |

FOREIGN PATENT DOCUMENTS

| EP | 3421002 A1 | 1/2019 |
| WO | 2019123170 A1 | 6/2019 |

OTHER PUBLICATIONS

ISR-WO from application PCT/IB2020/057695 dated Mar. 18, 2021 and that claims priority to the present US application.

* cited by examiner

*Primary Examiner* — Scott Luan

(74) *Attorney, Agent, or Firm* — Vorys, Sater, Seymour & Pease LLP

(57) ABSTRACT

A surgical tool includes a drive housing, a shaft extending from the drive housing, an end effector at an end of the shaft and having opposing jaws and a cutting element, and an articulable wrist configured to rotate the end effector within a plane. The wrist is articulated via antagonistic translation of a pair of drive members. Various systems are provided for homing one or more drive inputs that cause movement in the wrist and/or the end effector, or for controlling articulation of the drive inputs.

17 Claims, 20 Drawing Sheets

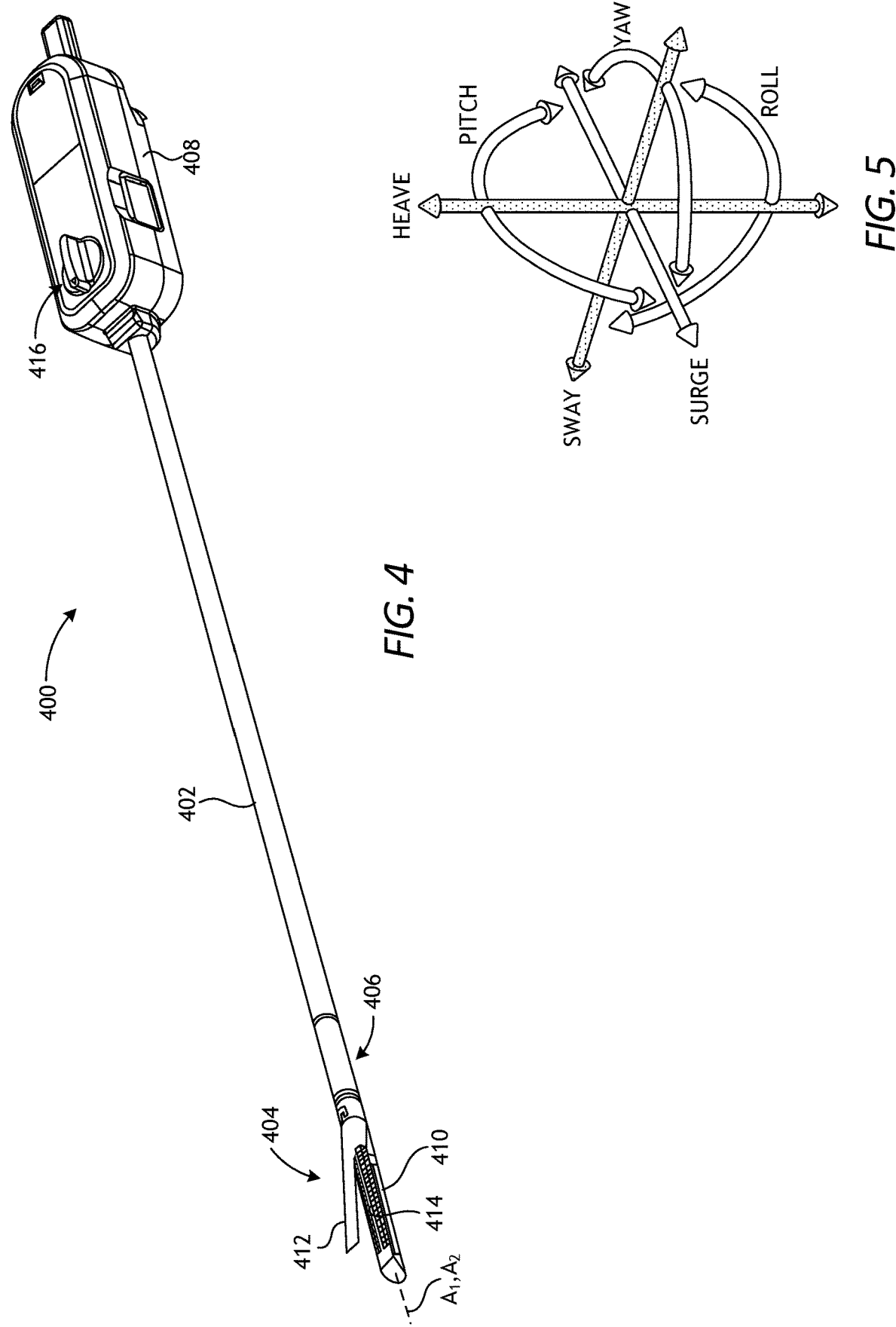

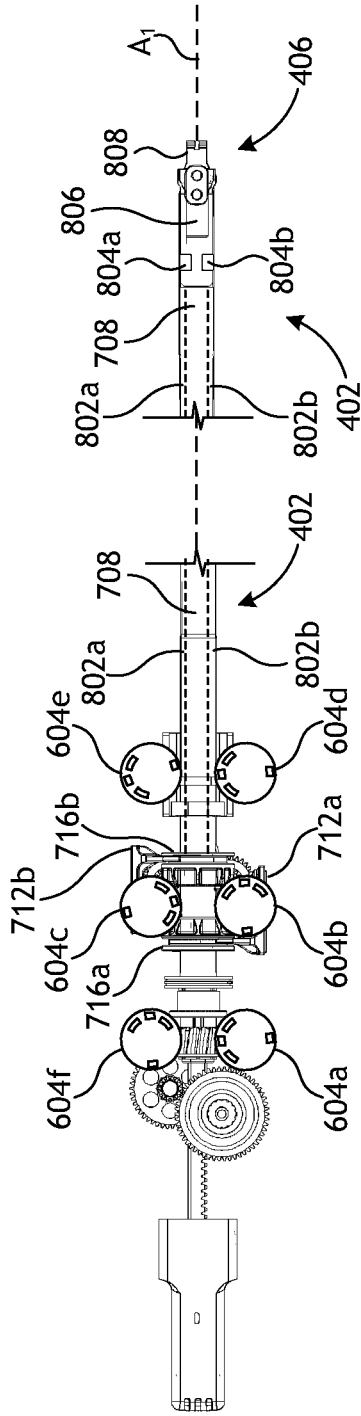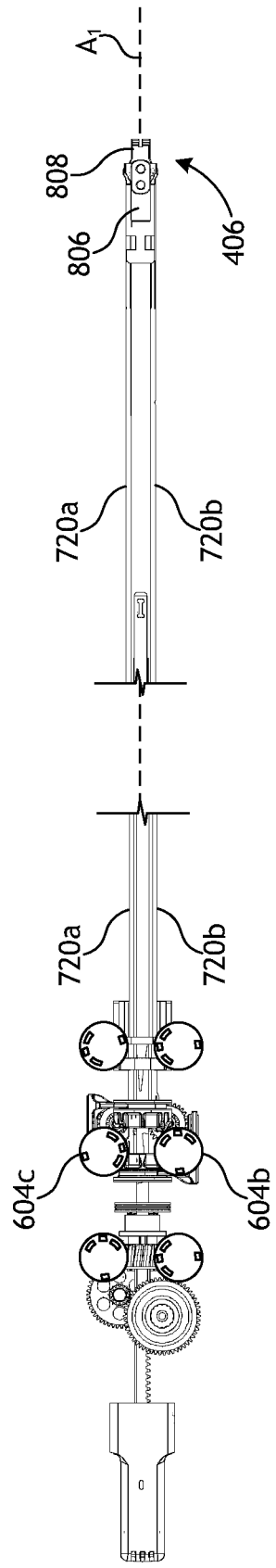
FIG. 9A
FIG. 9B

ARTICULATING INCLUDING ANTAGONISTIC CONTROLS FOR ARTICULATION AND CALIBRATION

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, and needle holders, and are similar to those used in conventional (open) surgery except that the end effector of each tool is separated from its handle by an approximately 12-inch long shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Surgical staplers are one type of end effector capable of cutting and simultaneously stapling (fastening) transected tissue. Alternately referred to as an "endocutter," the surgical stapler includes opposing jaws capable of opening and closing to grasp and release tissue. Once tissue is grasped or clamped between the opposing jaws, the end effector may be "fired" to advance a cutting element or knife distally to transect grasped tissue. As the cutting element advances, staples contained within the end effector are progressively deployed to seal opposing sides of the transected tissue.

Surgical tools include articulable wrists configured to permit angling of the end effector into a desired orientation. An articulable wrist having a joint that provides a high degree of freedom is needed. Also needed is a system for powering the articulable wrist such that it may move smoothly through tissue, which provides an external load on the wrist, and maintain a position into which it has been articulated when subjected to such external load. Moreover, systems for homing the drive inputs of the surgical are needed that, upon installing the surgical tool in the robotic manipulator, reposition the articulable wrist into an unarticulated orientation such that it may be inserted through a trocar and into the abdominal cavity.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 4 is an isometric side view of an example surgical tool that may incorporate some or all of the principles of the present disclosure.

FIG. 5 illustrates potential degrees of freedom in which the wrist of FIG. 4 may be able to articulate (pivot).

FIGS. 9A and 9B are exposed bottom views of the surgical tool of FIG. 4.

DETAILED DESCRIPTION

The present disclosure is related to robotic surgery and, more particularly, to an articulable wrist or joint used to position an end effector of a surgical tool, to systems for articulating the wrist into a desired position when subject to an external load and maintaining that position when subject to the load, systems for homing the articulable wrist, and systems for ensuring accurate positioning of the wrist.

Figure 1:
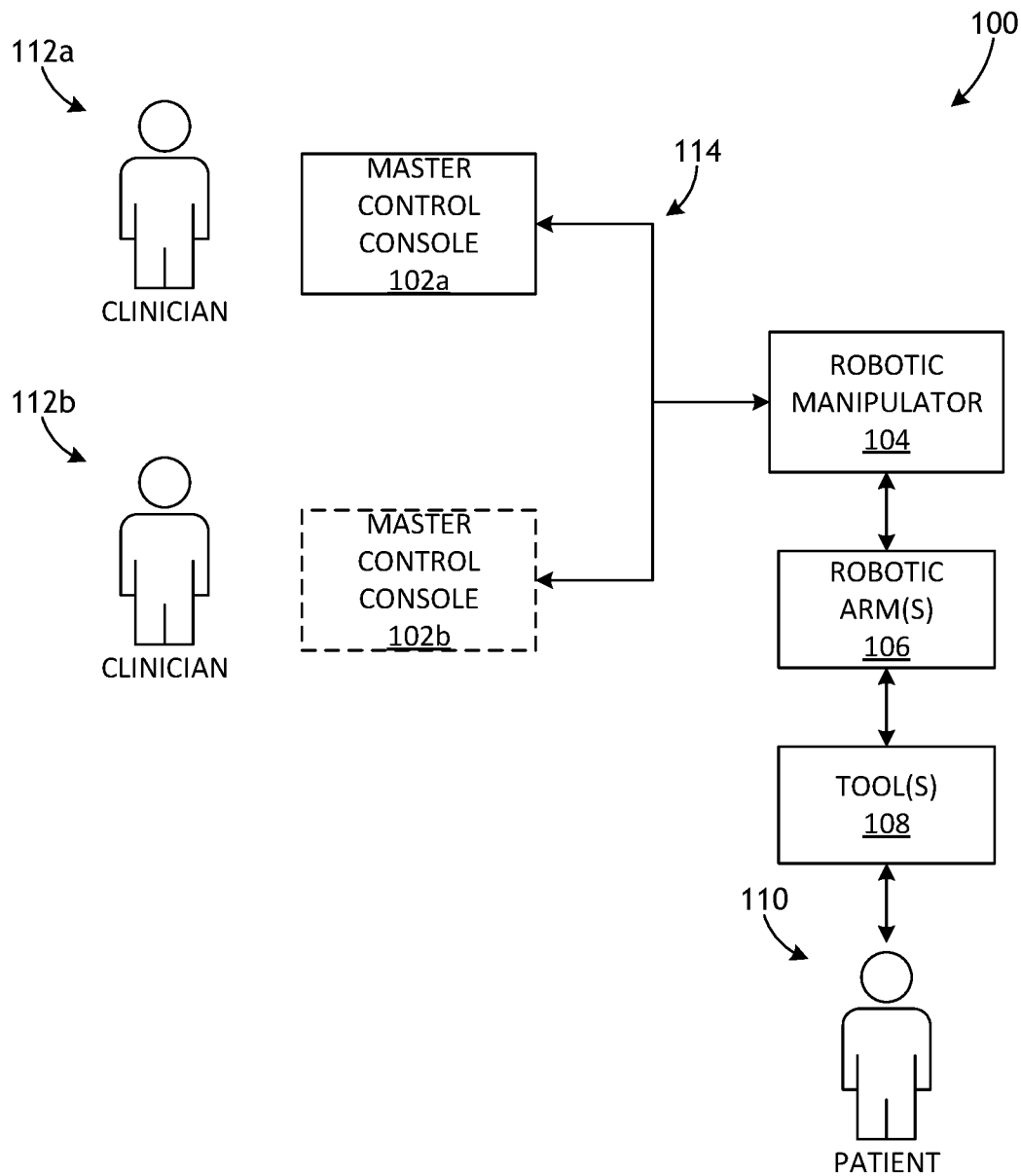
FIG. 1 is a block diagram of an example robotic surgical system that may incorporate some or all of the principles of the present disclosure.
Figure 3:
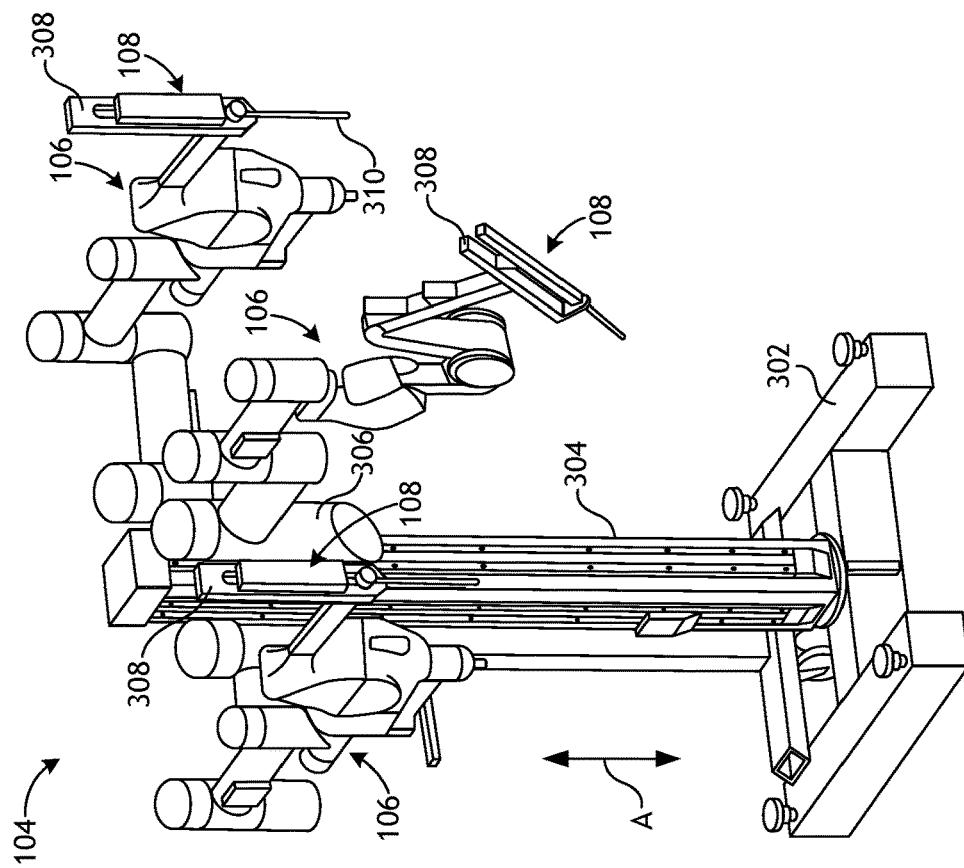
FIG. 3 depicts one example of the robotic manipulator of FIG. 1, according to one or more embodiments.
Figure 2:
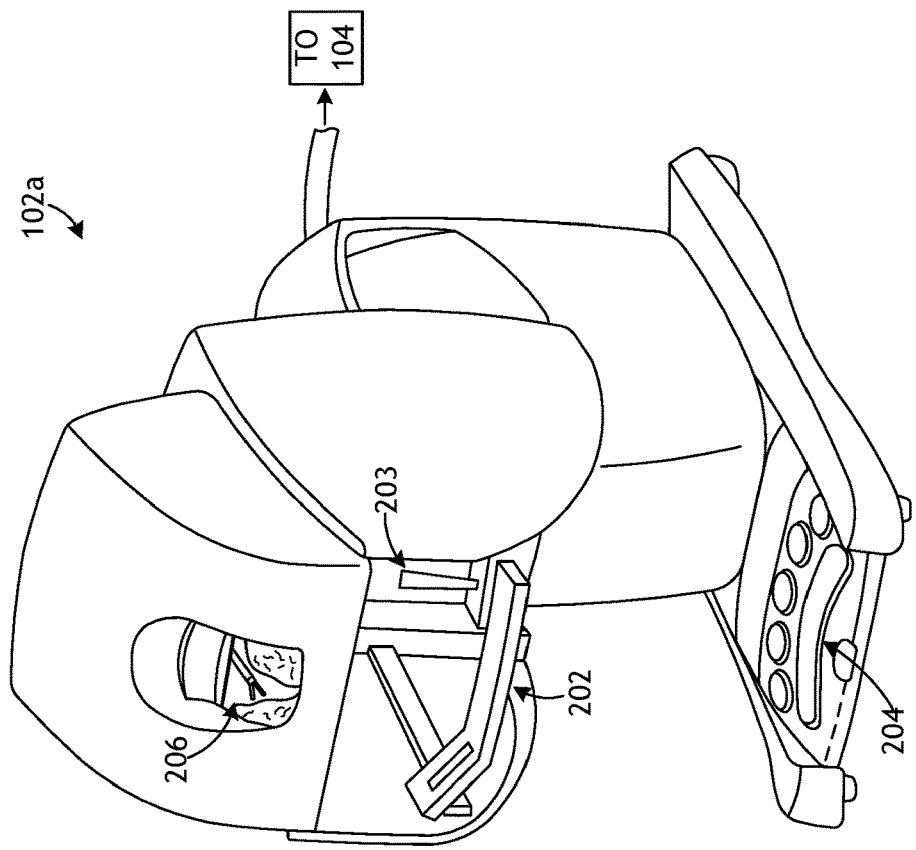
FIG. 2 is an example embodiment of one of the master control consoles of FIG. 1.

FIGS. 1-3 illustrate the structure and operation of an example robotic surgical system and associated components thereof. While applicable to robotic surgical systems, it is noted that the principles of the present disclosure may equally or alternatively be applied to non-robotic surgical systems, without departing from the scope of the disclosure.

FIG. 1 is a block diagram of an example robotic surgical system 100 that may incorporate some or all of the principles of the present disclosure. As illustrated, the system 100 can include at least one master control console 102a and at least one robotic manipulator 104. The robotic manipulator 104 may be mechanically and/or electrically coupled to or otherwise include one or more robotic arms 106. In some embodiments, the robotic manipulator 104 may be mounted to a transport cart (alternately referred to as an "arm cart") that enables mobility of the robotic manipulator 104 and the associated robotic arms 106. Each robotic arm 106 may include and otherwise provide a tool driver where one or more surgical instruments or tools 108 may be mounted for performing various surgical tasks on a patient 110. Operation of the robotic arms 106, the corresponding tool drivers, and the associated tools 108 may be directed by a clinician 112a (e.g., a surgeon) from the master control console 102a.

In some embodiments, a second master control console 102b (shown in dashed lines) operated by a second clinician 112b may also help direct operation of the robotic arms 106 and the tools 108 in conjunction with the first clinician 112a. In such embodiments, for example, each clinician 112a,b may control different robotic arms 106 or, in some cases, complete control of the robotic arms 106 may be passed between the clinicians 112a,b. In some embodiments, additional robotic manipulators having additional robotic arms may be utilized during surgery on a patient 110, and these additional robotic arms may be controlled by one or more of the master control consoles 102a,b.

The robotic manipulator 104 and the master control consoles 102a,b may communicate with one another via a communications link 114, which may be any type of wired or wireless communications link configured to carry suitable types of signals (e.g., electrical, optical, infrared, etc.) according to any communications protocol. The communications link 114 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network. Accordingly, the clinicians 112a,b may be able to remotely control the robotic arms 106 via the communications link 114, thus enabling the clinicians 112a,b to operate on the patient 110 remotely.

FIG. 2 is one example embodiment of the master control console 102a that may be used to control operation of the robotic manipulator 104 of FIG. 1. As illustrated, the master control console 102a can include a support 202 on which the clinician 112a,b (FIG. 1) can rest his/her forearms while gripping one or more user input devices 203, one in each hand. The user input devices 203 may comprise, for example, physical controllers such as, but not limited to, a joystick, exoskeletal gloves, a master manipulator, etc., and may be movable in multiple degrees of freedom to control the position, orientation, and operation of the surgical tool(s) 108 (FIG. 1). In some embodiments, the master control console 102a may further include one or more foot pedals 204 engageable by the clinician 112a,b to change the configuration of the surgical system and/or generate additional control signals to control operation of the surgical tool(s) 108.

The user input devices 203 and/or the foot pedals 204 may be manipulated while the clinician 112a,b (FIG. 1) views the procedure via a visual display 206. Images displayed on the visual display 206 may be obtained from an endoscopic camera or "endoscope." In some embodiments, the visual display 206 may include or otherwise incorporate a force feedback meter or "force indicator" that provides the clinician 112a,b with a visual indication of the magnitude of force being assumed by the surgical tool (i.e., a cutting instrument or dynamic clamping member) and in which direction. As will be appreciated, other sensor arrangements may be employed to provide the master control console 102a with an indication of other surgical tool metrics, such as whether a staple cartridge has been loaded into an end effector or whether an anvil has been moved to a closed position prior to firing, for example.

FIG. 3 depicts one example of the robotic manipulator 104 that may be used to operate a plurality of surgical tools 108, according to one or more embodiments. As illustrated, the robotic manipulator 104 may include a base 302 that supports a vertically extending column 304. A plurality of robotic arms 106 (three shown) may be operatively coupled to the column 304 at a carriage 306 that can be selectively adjusted to vary the height of the robotic arms 106 relative to the base 302, as indicated by the arrow A.

The robotic arms 106 may comprise manually articulable linkages, alternately referred to as "set-up joints." In the illustrated embodiment, a surgical tool 108 is mounted to corresponding tool drivers 308 provided on each robotic arm 106. Each tool driver 308 may include one or more drivers or motors (sometimes referred to as drivers 610a-f) used to interact with a corresponding one or more drive inputs of the surgical tools 108, and actuation of the drive inputs causes the associated surgical tool 108 to operate.

One of the surgical tools 108 may comprise an image capture device 310, such as an endoscope, which may include, for example, a laparoscope, an arthroscope, a hysteroscope, or may alternatively include some other imaging modality, such as ultrasound, infrared, fluoroscopy, magnetic resonance imaging, or the like. The image capture device 310 has a viewing end located at the distal end of an elongate shaft, which permits the viewing end to be inserted through an entry port into an internal surgical site of a patient's body. The image capture device 310 may be communicably coupled to the visual display 206 (FIG. 2) and capable of transmitting images in real-time to be displayed on the visual display 206.

The remaining surgical tools may be communicably coupled to the user input devices held by the clinician 112a,b (FIG. 1) at the master control console 102a (FIG. 2). Movement of the robotic arms 106 and associated surgical tools 108 may be controlled by the clinician 112a,b manipulating the user input devices. As described in more detail below, the surgical tools 108 may include or otherwise incorporate an end effector mounted on a corresponding articulable wrist pivotally mounted on a distal end of an associated elongate shaft. The elongate shaft permits the end effector to be inserted through entry ports into the internal surgical site of a patient's body, and the user input devices also control movement (actuation) of the end effector.

In use, the robotic manipulator 104 is positioned close to a patient requiring surgery and is then normally caused to remain stationary until a surgical procedure to be performed has been completed. The robotic manipulator 104 typically has wheels or castors to render it mobile. The lateral and vertical positioning of the robotic arms 106 may be set by the clinician 112a,b (FIG. 1) to facilitate passing the elongate shafts of the surgical tools 108 and the image capture device 310 through the entry ports to desired positions relative to the surgical site. When the surgical tools 108 and image capture device 310 are so positioned, the robotic arms 106 and carriage 306 can be locked in position.

FIG. 4 is an isometric side view of an example surgical tool 400 that may incorporate some or all of the principles of the present disclosure. The surgical tool 400 may be the same as or similar to the surgical tool(s) 108 of FIGS. 1 and 3 and, therefore, may be used in conjunction with a robotic surgical system, such as the robotic surgical system 100 of FIG. 1. As illustrated, the surgical tool 400 includes an elongated shaft 402, an end effector 404, an articulable wrist 406 (alternately referred to as a "wrist joint") that couples the end effector 404 to the distal end of the shaft 402, and a drive housing 408 coupled to the proximal end of the shaft 402. In applications where the surgical tool 400 is used in conjunction with a robotic surgical system, the drive housing 408 can include coupling features that releasably couple the surgical tool 400 to the robotic surgical system. The principles of the present disclosure, however, are equally applicable to surgical tools that are non-robotic and otherwise capable of manual manipulation.

The terms "proximal" and "distal" are defined herein relative to a robotic surgical system having an interface configured to mechanically and electrically couple the surgical tool 400 (e.g., the drive housing 408) to a robotic manipulator. The term "proximal" refers to the position of an element closer to the robotic manipulator and the term "distal" refers to the position of an element closer to the end effector 404 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 400 can have any of a variety of configurations capable of performing one or more surgical functions. In the illustrated embodiment, the end effector 404 comprises a surgical stapler, alternately referred to as an "endocutter," configured to cut and staple (fasten) tissue. As illustrated, the end effector 404 includes opposing jaws 410, 412 configured to move (articulate) between open and closed positions. The opposing jaws 410, 412, however, may alternately form part of other types of end effectors with jaws such as, but not limited to, a tissue grasper, surgical scissors, an advanced energy vessel sealer, a clip applier, a needle driver, a babcock including a pair of opposed grasping jaws, bipolar jaws (e.g., bipolar Maryland grasper, forceps, a fenestrated grasper, etc.), etc. One or both of the jaws 410, 412 may be configured to pivot to actuate the end effector 404 between the open and closed positions.

In the illustrated embodiment, the first jaw 410 may be characterized or otherwise referred to as a "cartridge" jaw, and the second jaw 412 may be characterized or otherwise referred to as an "anvil" jaw. More specifically, the first jaw 410 may include a frame that houses or supports a staple cartridge, and the second jaw 412 is pivotally supported relative to the first jaw 410 and defines a surface that operates as an anvil to form staples ejected from the staple cartridge during operation. In use, the second jaw 412 is rotatable between an open, unclamped position and a closed, clamped position. In other embodiments, however, the first jaw 410 may move (rotate) relative to the second jaw 412, without departing from the scope of the disclosure.

The wrist 406 enables the end effector 404 to articulate (pivot) relative to the shaft 402 and thereby position the end effector 404 at desired orientations and locations relative to a surgical site. FIG. 5 illustrates the potential degrees of freedom in which the wrist 406 may be able to articulate (pivot). The wrist 406 can have any of a variety of configurations. In general, the wrist 406 comprises a joint configured to allow pivoting movement of the end effector 404 relative to the shaft 402. The degrees of freedom of the wrist 406 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 404) with respect to a given reference Cartesian frame. As depicted in FIG. 5, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 406 (e.g., X-axis), yaw movement about a second axis of the wrist 406 (e.g., Y-axis), and combinations thereof to allow for 360° rotational movement of the end effector 404 about the wrist 406. In other applications, the pivoting motion can be limited to movement in a single plane, e.g., only pitch movement about the first axis of the wrist 406 or only yaw movement about the second axis of the wrist 406, such that the end effector 404 moves only in a single plane.

Referring again to FIG. 4, the surgical tool 400 may include a plurality of drive members or the like (obscured in FIG. 4) that form part of an actuation system configured to facilitate articulation of the wrist 406 and actuation (operation) of the end effector 404 (e.g., clamping, firing, rotation, articulation, energy delivery, etc.). Some drive members may extend to the wrist 406, and selective actuation of these drive members causes the end effector 404 to articulate (pivot) relative to the shaft 402 at the wrist 406. The end effector 404 is depicted in FIG. 4 in the unarticulated position where a longitudinal axis $A_2$ of the end effector 404 is substantially aligned with the longitudinal axis $A_1$ of the shaft 402, such that the end effector 404 is at a substantially zero angle relative to the shaft 402. In the articulated position, the longitudinal axes $A_1$, $A_2$ would be angularly offset from each other such that the end effector 404 is at a non-zero angle relative to the shaft 402.

Other drive members may extend to the end effector 404, and selective actuation of those drive members may cause the end effector 404 to actuate (operate). In the illustrated embodiment, actuating the end effector 404 may comprise closing and/or opening the second jaw 412 relative to the first jaw 410 (or vice versa), thereby enabling the end effector 404 to grasp (clamp) onto tissue. In addition, once tissue is grasped or clamped between the opposing jaws 410, 412, actuating the end effector 404 may further comprise "firing" the end effector 404, which may refer to causing a cutting element or knife (not visible) to advance distally within a slot 414 defined in the second jaw 410. As it moves distally, the cutting element may transect any tissue grasped between the opposing jaws 410, 412. Moreover, as the cutting element advances distally, a plurality of staples contained within the staple cartridge (i.e., housed within the first jaw 410) may be urged (cammed) into deforming contact with corresponding anvil surfaces (e.g., pockets) provided on the second jaw 412. The deployed staples may form multiple rows of staples that seal opposing sides of the transected tissue.

In some embodiments, the surgical tool 400 may be configured to apply energy to tissue, such as radio frequency (RF) energy. In such cases, actuating the end effector 404 may further include applying energy to tissue grasped or clamped between two opposing jaws to cauterize or seal the captured tissue, following which the tissue may be transected.

In some embodiments, the surgical tool 400 may further include a manual closure device 416 accessible to a user on the exterior of the drive housing 408. As illustrated, the manual closure device 416 may comprise a knob that may be grasped by the user. The manual closure device 416 may be operatively coupled to various gears and/or drive members within the drive housing 408 to allow a clinician to manually open and close the jaws 410, 412. In some cases, a clinician may be able to fully clamp and fully unclamp the jaws 410, 412 with the manual closure device 416. The manual closure device 416 may be particularly useful to a clinician when the surgical tool 400 is detached from a surgical robot, since having the capability to open and close the jaws 410, 412 may eliminate the need to place inadvertent stress on internal drive members or components. In the event that a clinician desires to manually open the jaws 410, 412 when the surgical tool 400 is still attached to a surgical robot, the clinician can rotate the manual closure device 416 in an attempt to open the end effector 404.

Figure 6:
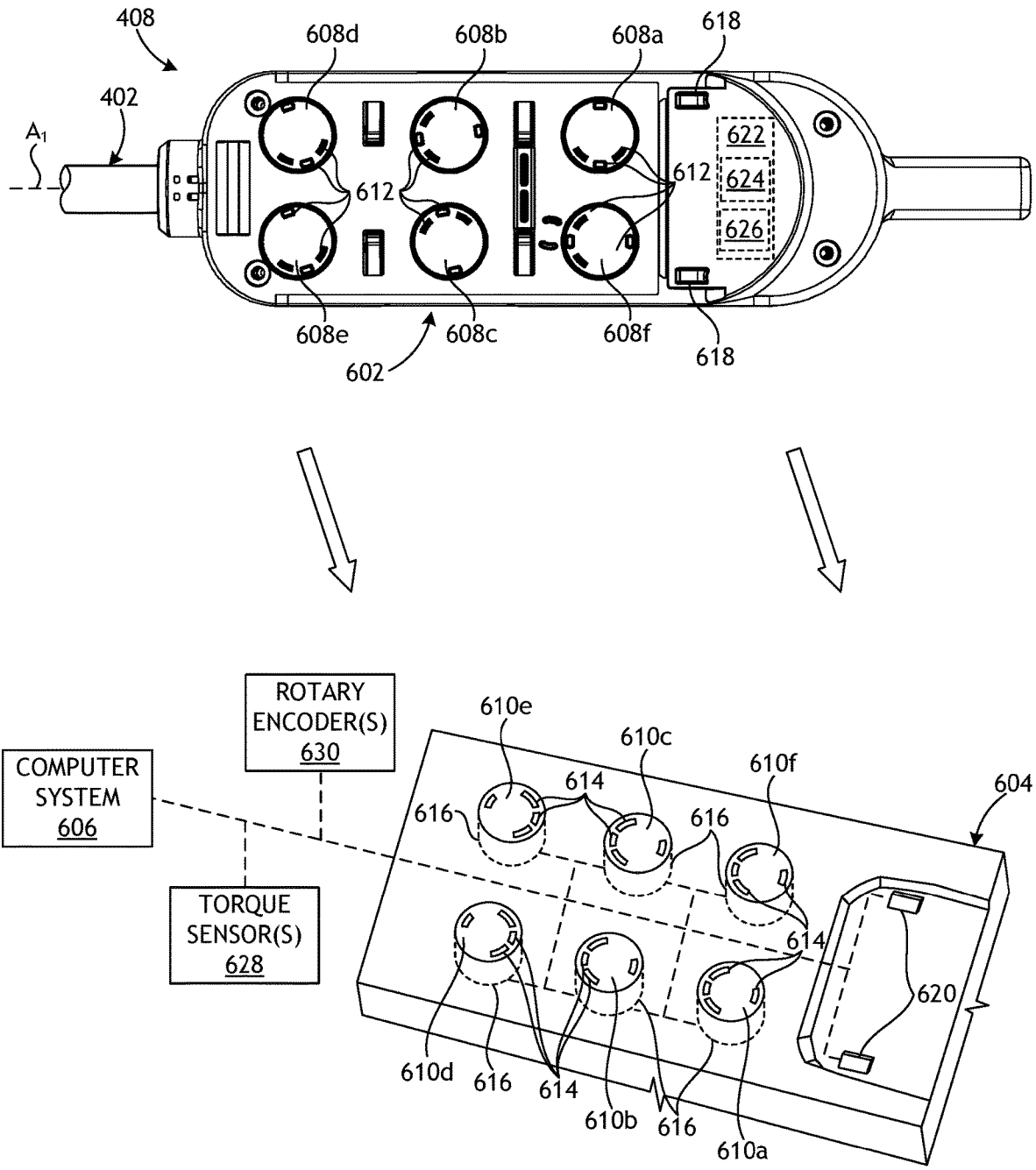
FIG. 6 is a bottom view of the drive housing of FIG. 4, according to one or more embodiments.

FIG. 6 depicts a bottom view of the drive housing 408, according to one or more embodiments. As illustrated, the drive housing 408 may include a tool mounting portion 602 used to operatively couple the drive housing 408 to a tool driver 604. The tool driver 604 may be the same as or similar to the tool drivers 308 of FIG. 3, and may thus be operable in conjunction with the robotic manipulator 104 of FIGS. 1 and 3. Mounting the drive housing 408 to the tool driver 604 places the drive housing 408 in communication with a computer system 606, which may communicate with or otherwise form part of the master controllers 102a,b (FIG. 1). The computer system 608 monitors and directs operation of the drive housing 408 via operation of the tool driver 604, thus enabling a user (e.g., the clinicians 112a,b of FIG. 1) to control operation of the drive housing 408 by working through the master controller 102a,b The tool mounting portion 602 includes and otherwise provides an interface that mechanically, magnetically, and/or electrically couples the drive housing 408 to the tool driver 604. In at least one embodiment, the tool mounting portion 602 couples the drive housing 408 to the tool driver 604 via a sterile barrier (not shown). As illustrated, the interface of the tool mounting portion 602 can include and support a plurality of inputs, shown as drive inputs 608a, 608b, 608c, 608d, 608e, and 608f. Each drive input 608a-f may comprise a rotatable disc or puck configured to align (mate) with and couple to a corresponding driver 610a, 610b, 610c, 610d, 610e, and 610f of the tool driver 604. Each drive input 608a-f and corresponding driver 610a-f provide or define one or more matable surface features 612 and 614, respectively, configured to facilitate mating engagement between the opposing surface features 612, 614 such that movement (rotation) of a given driver 610a-f correspondingly moves (rotates) the associated drive input 608a-f.

Each driver 610a-f of the tool driver 604 may include or otherwise comprise a motor 616 configured to actuate the corresponding driver 610a-f, and actuation of a given driver 610a-f correspondingly causes actuation of the mated drive input 608a-f, which facilitates operation of the mechanics of the drive housing 408. More specifically, actuation of the motors 616 may cause rotational movement of the corresponding driver 610a-f, which, in turn, rotates the associated drive input 608a-f. Each motor 616 may be in communication with the computer system 606 and, based on input signals provided by a user (e.g., a surgeon), the computer system 606 may selectively cause any of the motors 616 to actuate and thereby drive the corresponding driver 610a-f.

In some embodiments, actuation of the first drive input 608a via the first driver 610a may control rotation of the shaft 402 about its longitudinal axis $A_1$. Depending on the rotational direction of the first drive input 608a, the shaft 402 can be rotated clockwise or counter-clockwise, thus correspondingly rotating the end effector 404 (FIG. 4) in the same direction. Actuation of the second and third drive inputs 608b,c via the second and third drivers 610b,c, respectively, may control articulation of the end effector 404 at the wrist 406 (FIG. 4). Actuation of the fourth and fifth drive inputs 608d,e via the fourth and fifth drivers 610d,e, respectively, may cause an outer portion of the shaft 402 (referred to herein as a "closure tube") to advance and retract, which closes and opens the jaws 410, 412 (FIG. 4). Lastly, actuation of the sixth drive input 608f via the sixth driver 610f may cause the end effector 404 to fire, which may entail distal deployment of a cutting element to transect tissue grasped by the jaws 410, 412 and simultaneous deployment of staples contained within the staple cartridge housed within the first jaw 410.

The tool mounting portion 602 may further include one or more electrical connectors 618 (two shown) configured to mate with corresponding electrical connections 620 (two shown) provided by the tool driver 604 to facilitate communication between the drive housing 408 and the tool driver 604. Alternately, the drive housing 408 can wirelessly communicate with the tool driver 604, such as through a near field communication connection. The drive housing 408 may further house or otherwise include an internal computer 622 that may include a memory 624 and/or a microprocessor 626. The memory 624 may include one or more databases or libraries that store data relating to the drive housing 408 and, more particularly, to the surgical tool 400 (FIG. 4). In some embodiments, the memory 624 may include non-transitory, computer-readable media such as a read-only memory (ROM), which may be PROM, EPROM, EEPROM, or the like. Mating the drive housing 408 to the tool driver 604 places the internal computer 622 in communication with the computer system 606.

The computer system 606 may be programmed and otherwise configured to monitor operation of the surgical tool 400 (FIG. 4) using various sensors and/or electromechanical devices, collectively referred to herein as "monitoring devices." Each monitoring device may be designed to monitor one or more operational parameters of the surgical tool 400 and report measured operational parameters to the computer system 606 for processing. The computer system 606, for example, may be in communication with one or more torque sensors 628 and/or one or more rotary encoders 630, each of which may be characterized as a monitoring device designed to monitor operational parameters of the surgical tool 400. The torque sensors 628, for instance, may be configured to monitor torque, and the rotary encoders 630 may be configured to monitor motion (rotational or linear).

The torque sensors 628 and the rotary encoders 630 may be incorporated into the motors 616 of some or all of the drivers 610a-f, but could alternatively be operatively coupled to one or more of the drive inputs 608a-f. The torque sensors 628 may be configured to measure the real-time torque loading on the motors 616, which corresponds to the torque loading assumed by the drivers 610a-f and/or the drive inputs 608a-f. The rotary encoders 630 may measure the rotational motion or output of the motors 616, which corresponds to the rotational motion of the drivers 610a-f and/or the drive inputs 608a-f. Monitoring torque loading and rotational motion of the motors 616 may help determine if the surgical tool 400 is operating in accordance with the commands provided by the computer system 606.

Referring to FIGS. 7A and 7B and FIGS. 8A and 8B, illustrated are exposed isometric views of the interior of the drive housing 408, according to one or more embodiments. The upper portion of the drive housing 408 is omitted in FIGS. 7A-7B to allow viewing of the internal working components and parts, and both the upper and lower portions of the drive housing 408 are omitted in FIGS. 8A-8B to allow viewing of the internal working components and parts. In addition, several component parts that would otherwise be included within the drive housing 408 are omitted in FIGS. 7A-7B and 8A-8B to simplify the figures and enable discussion of the depicted component parts.

Figure 7A:
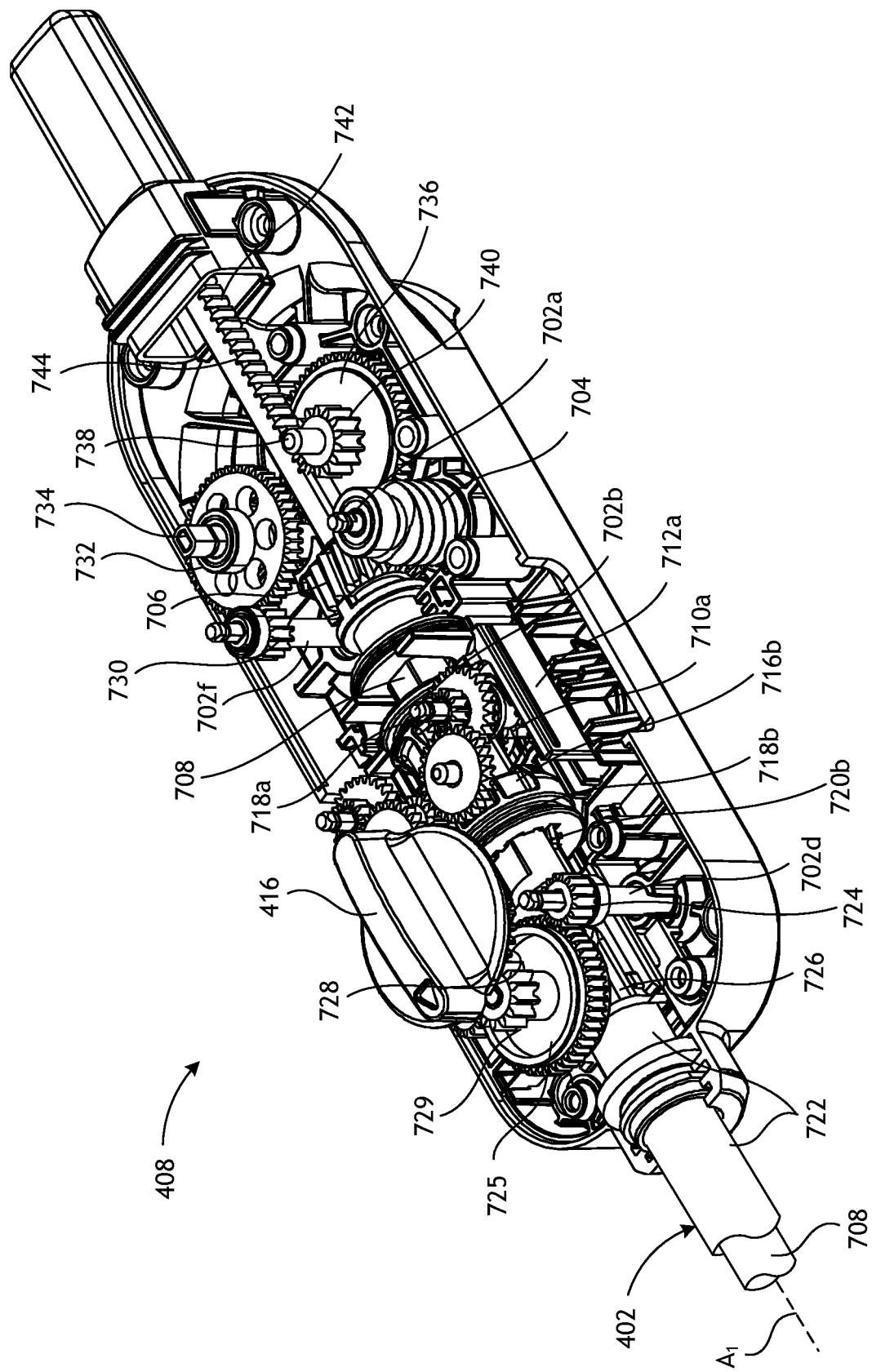
FIGS. 7A and 7B are exposed isometric views of the interior of the drive housing of FIG. 4, according to one or more embodiments.
Figure 7B:
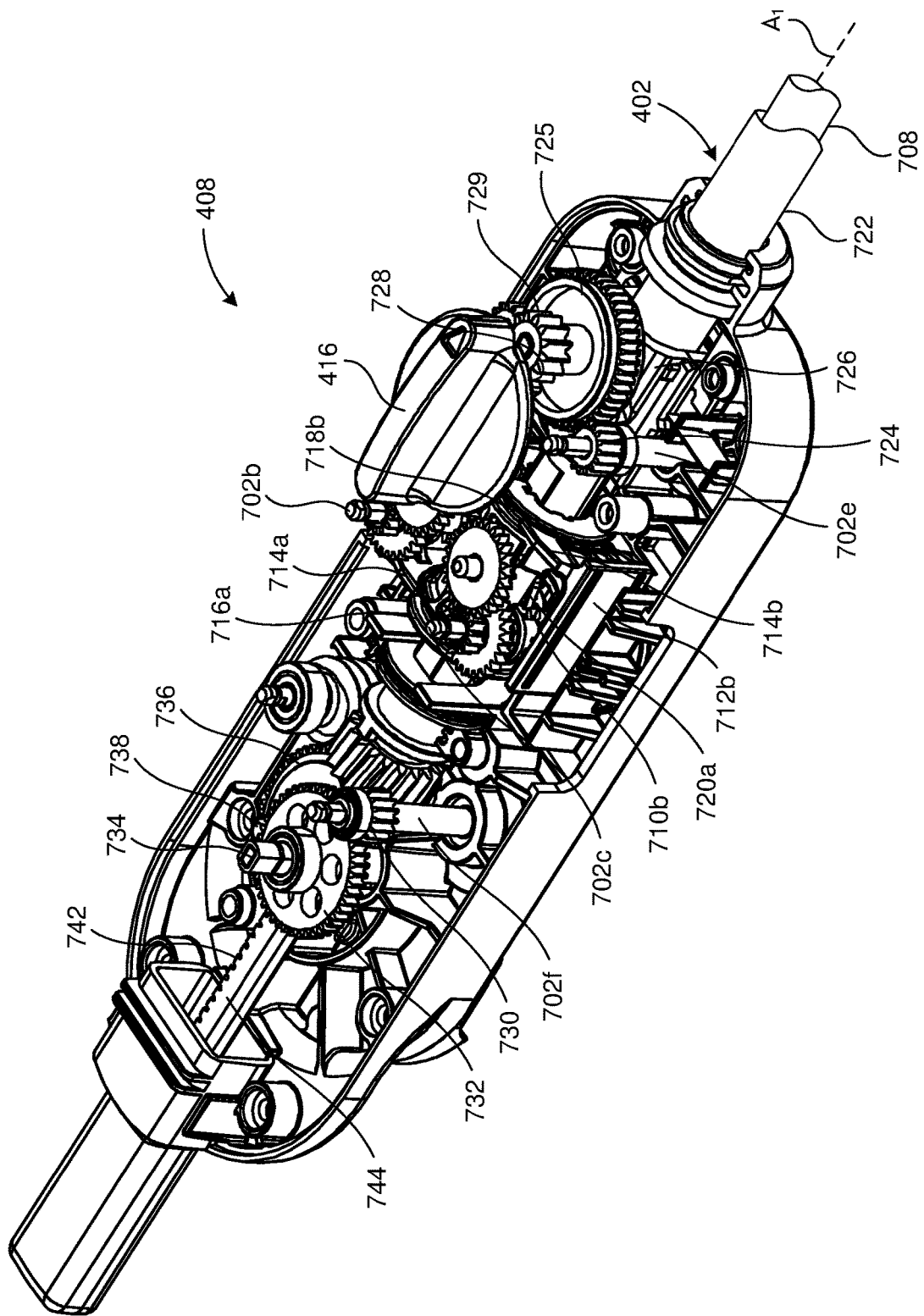

Referring first to FIG. 7A, a first drive shaft 702a is coupled to the first drive input 608a (FIG. 6) such that actuation and rotation of the first drive input 608a correspondingly rotates the first drive shaft 702a. A helical drive gear 704 is coupled to the first drive shaft 702a and rotates as the first drive shaft 702a rotates. The helical drive gear 704 intermeshes with a helical driven gear 706, which is operatively coupled to the shaft 402 and, more particularly, to an inner grounding member or shaft 708 that forms part of the shaft 402. The inner grounding shaft 708 extends concentrically within an outer portion of the shaft 402 referred to herein as the "closure tube." Accordingly, actuation of the first drive input 608a drives the first drive shaft 702a and correspondingly drives the inner grounding shaft 708 to rotate the shaft 402 about the longitudinal axis $A_1$.

A second drive shaft 702b may be coupled to the second drive input 608b (FIG. 6) such that actuation and rotation of the second drive input 608b correspondingly rotates the second drive shaft 702b. In some examples, a drive train or gearing may be provided to adjust the mechanical advantage output from one or more motors of the robotic manipulator (not illustrated). For example, if the second driver 610b (FIG. 6) outputs relatively low torque, one or more intermeshed gears may be utilized to increase the torque imparted by the second driver 610b on the drive shaft 702b. As best exemplified in FIGS. 8A-8B, a spur gear 709a is attached and keyed to the second drive shaft 702b such that the spur gear 709a rotates in unison with drive shaft 702b. Also, a compound pinion gear 710a is rotatably attached to the second drive shaft 702b, such that the compound pinion gear 710a is rotatable about and relative to the second drive shaft 702b. As illustrated, the compound pinion gear 710a includes a first pinion gear 711a and a second pinion gear 713a that are rigidly connected together such that they rotate together about the second drive shaft 702b. The second pinion gear 713a of the compound pinion gear 710a intermeshes with a first driven rack 712a such that, as the compound pinion gear 710a is rotated in a first rotational direction, the first driven rack 712a correspondingly translates in a first longitudinal direction; and, as the compound pinion gear 710a is rotated in a second rotational direction, the first driven rack 712a correspondingly translates in a second longitudinal direction opposite the first longitudinal direction.

In addition, an idler assembly 715a (FIGS. 8A-8B) is provided to transfer rotation of the second drive shaft 702b to the compound pinion gear 710a and thereby effectuate translation of the first driven rack 712a in the first or second longitudinal direction. In the illustrated example, the idler assembly 715a is a compound gear having a first idler 717a and a second idler 719a that is rigidly connected to the first idler 717a such that they rotate together in unison. Here, the first idler 717a meshes with the spur gear 709a that is keyed to the second drive shaft 702b, and the second idler 719a meshes with the first pinion gear 711a of the compound pinion gear 710a to thereby drive the first driven rack 712a. Thus, the second driver 610b (FIG. 6) rotates the second drive input 608b, which in turn rotates the second drive shaft 702b and the spur gear 709a connected thereto. The spur gear 709a imparts rotation to the first idler 717a of the idler assembly 715a, which in turn also imparts rotation on the second idler 719a thereof as it is keyed to the first idler 717a. The second idler 719a of the idler assembly 715a imparts rotation on the first pinion gear 711a of the compound pinion gear 710a, which in turn also imparts rotation on the second pinion gear 713a of the compound pinion gear 710a as it is keyed to the first pinion gear 711a. As described above, such rotation of the second pinion gear 713a causes translation of the first drive rack 712a.

The illustrated drive train transferring power between the second driver 610b (FIG. 6) and the first driven rack 712a is configured with a cumulative gear ratio that increases the torque that the compound pinion gear 710a exerts on the first drive rack 712a beyond what is initially applied to the drive input 608b by the second driver 610b. In particular, because the spur gear 709a is smaller (i.e., less teeth) than the first idler 717a with which it meshes and because the second idler 719a is smaller (i.e., less teeth) than the first pinion gear 711 with which it meshes, the torque acting on the compound pinion gear 710a that drives the first drive rack 712a is significantly larger than the torque initially applied on the second drive shaft 702b via the second driver 610b.

Figure 8A:
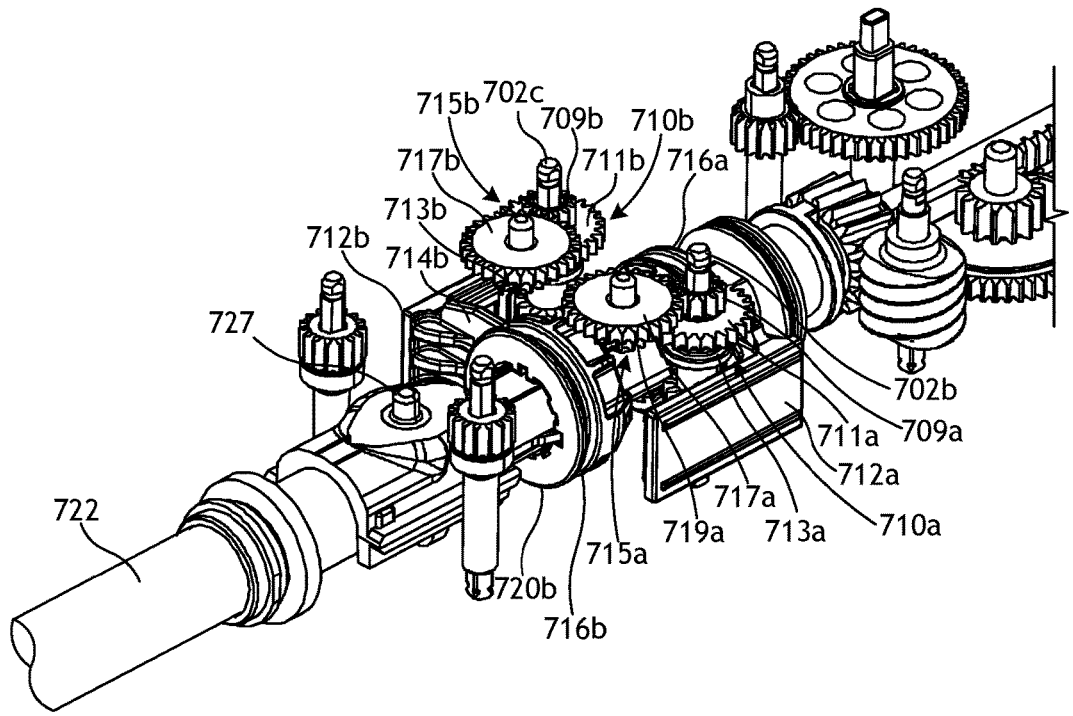
FIGS. 8A and 8B are exposed isometric views depicting example gear trains within the surgical tool of FIGS. 7A-7B.
Figure 8B:
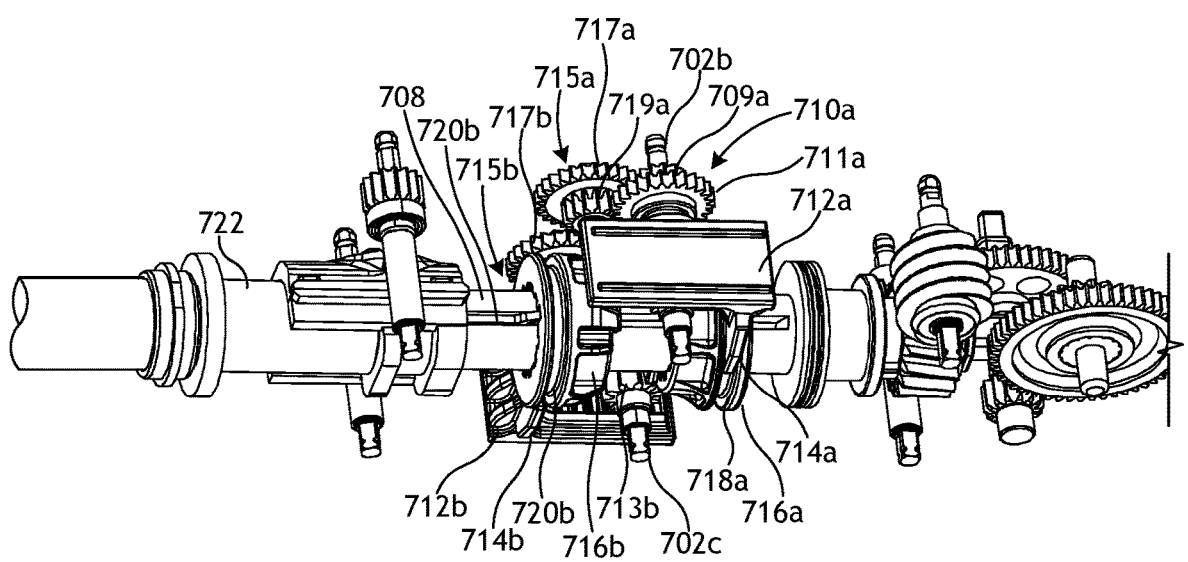

The first driven rack 712a includes a first fork 714a matable with a first articulation yoke 716a. More specifically, the first fork 714a is configured to be received within an annular slot 718a (FIGS. 7A and 8B) defined in the first articulation yoke 716a, which allows the first articulation yoke 716a to rotate about the longitudinal axis $A_1$ as the inner grounding shaft 708 rotates. Moreover, engagement between the first fork 714a and the annular slot 718a allows the first driven rack 712a to drive the first articulation yoke 716a along the longitudinal axis $A_1$ (distally or proximally) as acted upon by rotation of the second drive shaft 702b. The first articulation yoke 716a may be coupled to a first drive member 720a, which extends distally to the wrist 406 (FIG. 4). As illustrated, the first drive member 720a is arranged within a corresponding slot defined in the inner grounding shaft 708, such that the inner grounding shaft 708 guides the first drive member 720a as they extend distally together to the wrist 406 (FIG. 8). Axial movement of the first articulation yoke 716a along the longitudinal axis $A_1$ correspondingly moves the first drive member 720a, which causes the wrist 406 and the end effector 404 (FIG. 4) to articulate.

A third drive shaft 702c is coupled to the third drive input 608c (FIG. 6) such that actuation and rotation of the third drive input 608c correspondingly rotates the third drive shaft 702c. Similar to the description of the second drive shaft 702b coupled to the second drive input 608b, a drive train or gearing may be provided to adjust mechanical advantage and thus vary the torque or speed initially applied by the third driver 610c (FIG. 6) to the third drive shaft 702c. In the illustrated example, a spur gear 709b is attached and keyed to the third drive shaft 702c such that the spur gear 709b rotates in unison with third drive shaft 702c. A compound pinion gear 710b is rotatably attached to the third drive shaft 702c such that the compound pinion gear 710b may rotate about and relative to the third drive shaft 702c. As illustrated, the compound pinion gear 710b includes a first pinion gear 711b and a second pinion gear 713b that are rigidly connected together such that they rotate together about the third drive shaft 702*c*. The second pinion gear 713*b* of the compound pinion gear 710*b* intermeshes with a second driven rack 712*b* such that rotating the compound pinion gear 710*b* in a first rotational direction correspondingly translates the second driven rack 712*b* in a first longitudinal direction. Rotating the compound pinion gear 710*b* in a second rotational direction correspondingly translates the second driven rack 712*b* in a second longitudinal direction opposite the first longitudinal direction.

In addition, an idler assembly 715*b* is provided to transfer rotation of the third drive shaft 702*c* to the compound pinion gear 710*b* and thereby effectuate translation of the second driven rack 712*b* in the first or second longitudinal direction. In the illustrated example, the idler assembly 715*b* is a compound gear having a first idler 717*b* and a second idler 719*b* that is rigidly connected to the first idler 717*b* such that they rotate together in unison. Here, the first idler 717*b* meshes with the spur gear 709*b* that is keyed to the third drive shaft 702*c*, and the second idler 719*b* meshes with the first pinion gear 711*b* of the compound pinion gear 710*b* to thereby drive the second driven rack 712*b*. Thus, the third driver 610*c* (FIG. 6) rotates the third drive input 608*c*, which in turn rotates the third drive shaft 702*c* and the spur gear 709*b* connected thereto. The spur gear 709*b* imparts rotation to the first idler 717*b* of the idler assembly 715*b*, which in turn also imparts rotation on the second idler 719*b* thereof as it is keyed to the first idler 717*b*. The second idler 719*b* of the idler assembly 715*b* imparts rotation on the first pinion gear 711*b* of the compound pinion gear 710*b*, which in turn also imparts rotation on the second pinion gear 713*b* of the compound pinion gear 710*b* as it is keyed to the first pinion gear 711*b*. As described above, such rotation of the second pinion gear 713*b* causes translation of the first drive rack 712*b*. The illustrated drive train transferring power between the third driver 610*c* and the second driven rack 712*b* is configured with a cumulative gear ratio that results in increased output torque acting on the compound pinion gear 710*b* and thereby exerted on the second drive rack 712*b* beyond what is initially applied to the third drive input 608*c* by the third driver 610*c*.

The second driven rack 712*b* includes a second fork 714*b* matable with a second articulation yoke 716*b*. More particularly, the second fork 714*b* is configured to be received within an annular slot 718*b* defined in the second articulation yoke 716*b*, which allows the second articulation yoke 716*b* to rotate about the longitudinal axis $A_1$ as the inner grounding shaft 708 rotates. Moreover, engagement between the second fork 714*b* and the annular slot 718*b* allows the second driven rack 712*b* to drive the second articulation yoke 716*b* along the longitudinal axis $A_1$ (distally or proximally) as acted upon by rotation of the third drive shaft 702*c*. The second articulation yoke 716*b* may be coupled to a second drive member 720*b* (FIG. 7A), which extends distally to the wrist 406 (FIG. 4). The second drive member 720*b* is arranged within a corresponding slot defined in the inner grounding shaft 708, such that the inner grounding shaft 708 guides the second drive member 720*b* as they extend distally together to the wrist 406 (FIG. 8). Axial movement of the second articulation yoke 716*b* along the longitudinal axis $A_1$ correspondingly moves the second drive member 720*b*, which causes the wrist 406 and the end effector 404 (FIG. 4) to articulate.

Accordingly, axial movement of the first and second articulation yokes 716*a,b*, along the longitudinal axis $A_1$ cooperatively actuates the drive members 720*a,b* and, thereby, articulates the end effector 404 as further described herein with reference to FIGS. 9A-9B and 10A-10B. In at least one embodiment, the first and second articulation yokes 716*a,b* protagonistically operate such that one of the articulation yokes 716*a,b* pulls one of the drive members 720*a,b* proximally while the other articulation yoke 716*a,b* pushes the other drive member 720*a,b* distally. In some embodiments, however, the first and second articulation yokes 716*a,b* may be operated independently without the other being operated (affected), for example, they may operate antagonistically where one reduces the force effect of another. In antagonistic operation, one of the articulation yokes 716*a,b* pulls (or pushes) the drive member 720*a,b* associated therewith proximally (or distally) with a first force while the other one of the articulation yokes 716*a,b* pulls (or pushes) the drive member 720*a,b* associated therewith proximally (or distally) with a second force, where the first force is larger than the second force such that the first force can overcome the second force, as well as the internal losses of the device (i.e., friction) and loads imparted on the end effector 404 via the external environment, thereby ensuring that the articulation yoke 716*a,b* providing the first force moves proximally (or distally) while the articulation yoke 716*a,b* providing the second force moves distally (or proximally). As described below, the computer system 606 (FIG. 6) may be configured to control the drivers 610*b,c* (FIG. 6) that drive the drive inputs 608*b-c* and interconnected drive shafts 702*b-c* to thereby synchronize actuation of the articulation yokes 716*a,b*.

A fourth drive shaft 702*d* (FIG. 7A) and a fifth drive shaft 702*e* (FIG. 7B) may be coupled to the fourth and fifth drive inputs 608*d,e* (FIG. 6), respectively, such that actuation and rotation of the fourth and fifth drive inputs 608*d,e* correspondingly rotates the fourth and fifth drive shafts 702*d,e*. Rotation of the fourth and fifth drive shafts 702*d,e* may cause a portion of the shaft 402 to advance or retract. More specifically, the outer portion of the shaft 402 may comprise a closure tube 722 that is axially translated to move the jaws 410, 412 (FIG. 4) between open and closed positions. As illustrated, each drive shaft 702*d,e* has a spur gear 724 attached thereto, and both spur gears 724 are positioned to mesh with a primary drive gear 725 mounted to a closure yoke 726.

The closure yoke 726 is rotatably mounted to the closure tube 722 but fixed axially thereto. This allows the closure tube 722 to rotate as the inner grounding shaft 708 rotates, but also allows the closure yoke 726 to advance or retract the closure tube 722. A projection 727 (FIG. 8A) extends from or is otherwise coupled to the closure yoke 726, and the projection interacts with a camming surface or slot defined within the primary drive gear 725 to facilitate axial movement of the closure yoke 726. Accordingly, rotating the spur gears 724 causes the primary drive gear 725 to rotate, which correspondingly causes the closure yoke 726 and the interconnected closure tube 722 to axially translate.

The primary drive gear 725 may also be operatively coupled to the manual closure device 416 arranged on the exterior of the drive housing 408. As illustrated, the manual closure device 416 may include a drive gear 728 that intermeshes with a driven gear 729 mounted to the primary drive gear 725. Consequently, a user can grasp and rotate the manual closure device 416 to correspondingly rotate the primary drive gear 725 and thereby drive the drive gear 728 against the driven gear 729 to move the closure yoke 426 distally and proximally to close and open the jaws 410, 412 (FIG. 4), as generally described above. In one example, the primary drive gear 725 is intermeshed between the spur gears 724 and comprises a central aperture that rotatably mounts the primary drive gear 725 within the drive housing 408 (FIGS. 7A-7B) relative to the spur gears 724. A spiral cam slot is defined in the primary drive gear 725 and the projection 727 (FIG. 8A) of the closure yoke 726 (FIGS. 7A-7B) is received therein. The primary drive gear 725 is rotatable about an axis extending through the central aperture as acted upon by the spur gears 724. As the primary drive gear 725 rotates, the projection follows the spiral cam slot, and the curvature of the spiral cam slot urges the interconnected closure yoke 726 to translate longitudinally relative to the primary drive gear 725. When the closure yoke 726 moves distally, the closure tube 722 (FIGS. 7A-7B) correspondingly moves in the distal direction and causes the jaws 410, 412 (FIG. 4) to close. In contrast, when the closure yoke 726 moves proximally, the closure tube 722 correspondingly moves in the proximal direction and causes the jaws 410, 412 to open.

FIGS. 9A and 9B illustrate exposed bottom views of the surgical tool 400, according to one or more embodiments. Much of the gearing and actuation mechanisms described above are depicted, but the entirety of the drive housing 408 and the closure tube 722 of the shaft 402 are omitted in FIGS. 9A-9B to allow viewing of the internal working components and parts utilized to articulate the drive members 720*a,b* and the wrist 406. In addition, several component parts that would otherwise be included within the drive housing 408 are omitted in these figures to simplify the figures and enable discussion of the depicted component parts.

With reference to FIG. 9A, the inner grounding shaft 708 extends distally within the shaft 402 and is connected to the wrist 406. The drive members 720*a,b* (FIG. 9B) extend distally towards the wrist 406 within corresponding slots 802*a,b* (shown as dashed lines in FIG. 9A) defined within the inner grounding shaft 708. The corresponding slots 802*a,b* may be provided on opposite sides of the inner grounding shaft 708, or may be defined elsewhere about the inner grounding shaft 708 in other examples. As described below, movement of the drive members 720*a,b* articulates the wrist 406. Also, the inner grounding shaft 708 is configured to effect rotation of the wrist 406 about the longitudinal axis $A_1$, even when the wrist 406 is articulated to an angularly offset position relative to the longitudinal axis $A_1$.

In the illustrated example, a locking or grounding recess (obscured from view) is formed into a bottom side of the distal end of the inner grounding shaft 708, and the grounding recess defines a pair of locking tabs 804*a,b* configured to interlock with other componentry of the wrist 406. Here, a base 806 of the wrist 406 is integrally secured within the grounding recess of the inner grounding shaft 708 via the locking tabs 804*a,b* such that the inner grounding shaft 708 carries the wrist 406 as it rotates about the longitudinal axis $A_1$ upon actuation of the first drive input 608*a*. In addition, the slots 802*a,b* extend through the grounding recess and the locking tabs 804*a,b*, with lower boundary of the slots 802*a,b* being defined by an upper surface of the base 806, as described below.

The wrist 406 further includes an articulation member 808 to which the end effector 404 may be mounted. The articulation member 808 is coupled to the base 806 and the drive members 720*a,b*, such that movement of the drive members 720*a,b* articulates the articulation member 808 relative to the base 806. Thus, the wrist 406 and the end effector 404 extending distally therefrom may be angularly offset via movement of the drive members 720*a,b*.

In FIG. 9B the inner grounding shaft 708 has been removed. As illustrated, the drive members 720*a,b* are interconnected at their distal ends via a third link member, described herein with reference to FIG. 10B and referred to herein as a "distal link." Thus, the drive members 720*a,b* and the distal link together comprise a linkage configured to articulate the articulation member 808 relative to the base 806 in a plane parallel to the longitudinal axis $A_1$. With this configuration, the drive members 720*a,b* translate antagonistically within their corresponding slots 802*a,b* (FIG. 9A) along the longitudinal axis $A_1$, such that as the first drive member 720*a* moves distally the second drive member 702*b* moves proximally, and vice versa. More specifically, distal movement of the first drive member 720*a* acts on the articulation member 808 and causes the articulation member 808 to rotate clockwise and thereby push the second drive member 720*b* proximally. Thus, the first drive member 720*a* moves distally as the second drive member 720*b* moves proximally, thereby causing the wrist 406 to articulate in the plane such that it is angularly offset at a non-zero angle relative to the inner grounding shaft 708. As mentioned above, the wrist 406 is also configured to rotate with the inner grounding shaft 708 about the longitudinal axis $A_1$, and thereby rotate the plane in which the articulation member 808 articulates (360° about the longitudinal axis $A_1$).

Figure 10A:
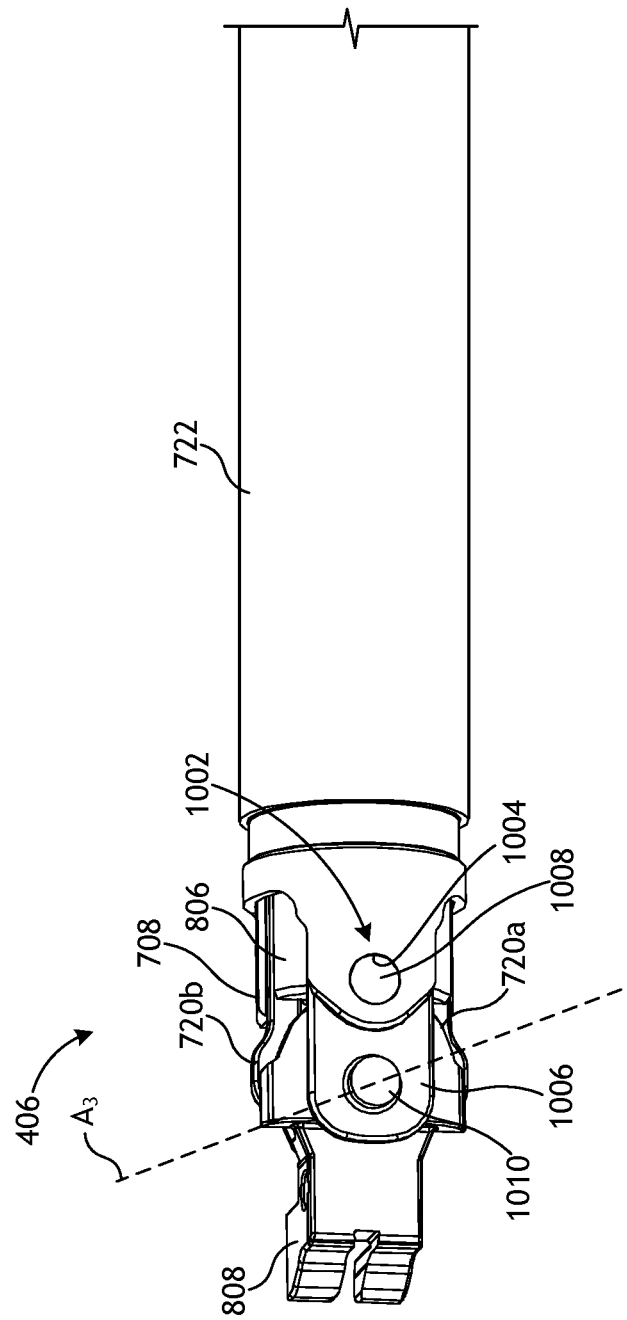
FIG. 10A illustrates an example articulable wrist that may be utilized in the surgical tool of FIGS. 9A and 9B, according to one or more embodiments of the disclosure.

FIG. 10A illustrates a bottom view of the wrist 406, according to one or more embodiments. As illustrated, the base 806 is attached to the inner grounding shaft 708 and arranged within the closure tube 722. Here, the closure tube 722 includes a distal clevis 1002 having a pair of apertures 1004. In addition, a closure link 1006 having a pair of pins 1008, 1010 is provided and, when the base 806 and the inner grounding shaft 708 are arranged within the closure tube 722, the first pin 1008 of the closure link 1006 is received within one of the apertures 1004 in the distal clevis 1002. The closure link 1006 is utilized to transmit closure action around the articulation joint. For example, the closure link 1006 may transmit the closure load or translation of the closure tube 722 to a closure ring (not illustrated) that may be coupled to the second pin 1010 of the closure link 1006, which pulls or pushes the upper jaw (anvil) open or closed. Also, the articulation member 808 is able to rotate about an articulation axis $A_3$ that, in the illustrated example, is shown extending through the second pin 1010 of the closure link 1006.

Figure 10B:
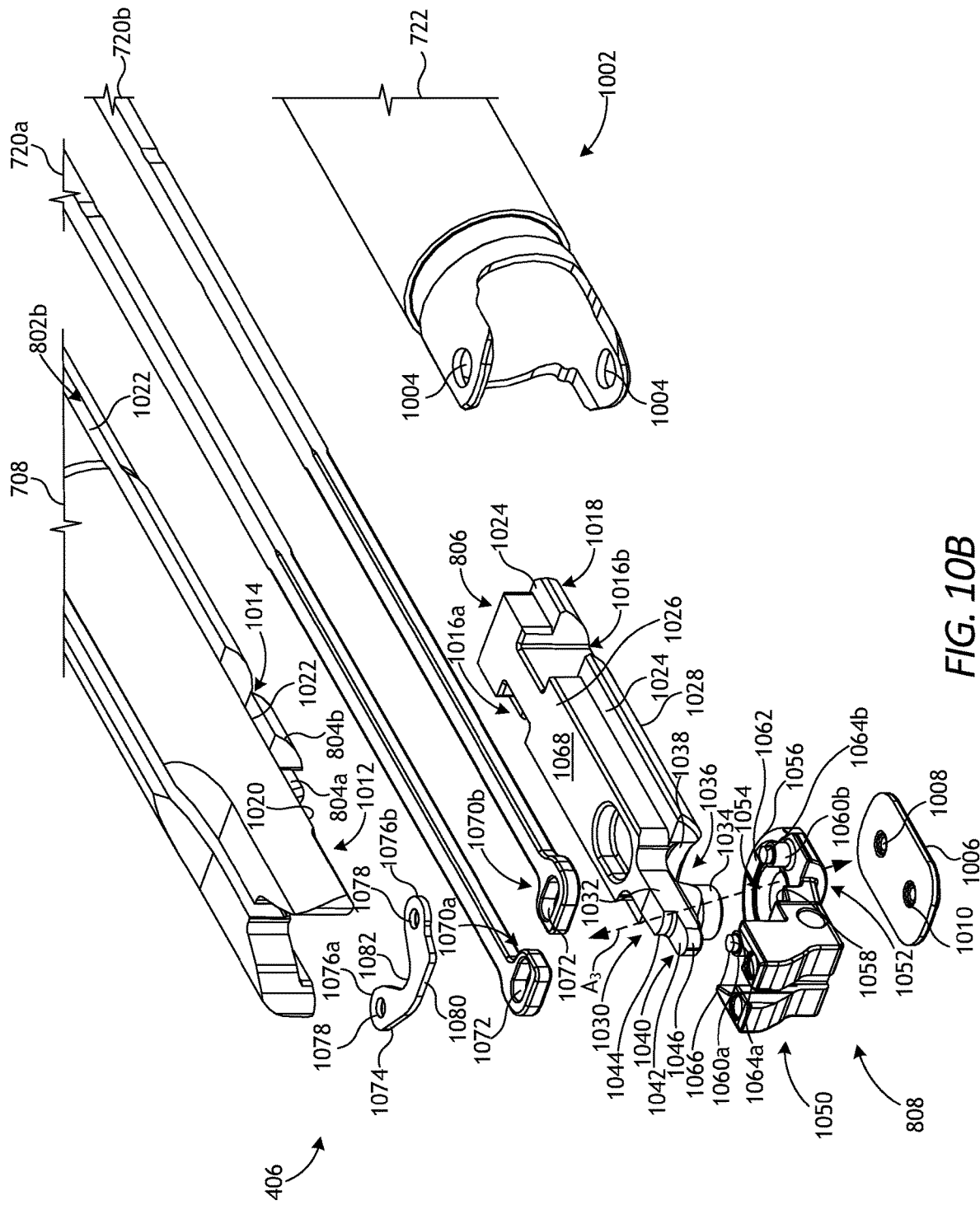
FIG. 10B is an exploded view of the articulable wrist of FIG. 10A, according to one or more embodiments of the disclosure.

FIG. 10B illustrates an exploded isometric view of the wrist 406 of FIG. 10A. As mentioned, the grounding member 708 includes a grounding recess configured to rigidly secure the base 806 thereto. As illustrated, the inner grounding shaft 708 includes a pair of grounding recesses 1012, 1014 formed into a distal end of the inner grounding shaft 708. As shown, the grounding recesses 1012, 1014 define or provide the locking tabs 804*a,b* configured to engage the base 806 and inhibit relative rotation there-between. In the illustrated example, the base 806 includes a pair of notches 1016*a* and 1016*b* configured to receive the locking tabs 804*a,b*, and the pair of notches 1016*a,b* define a proximal locking flange 1018 configured to be received within the grounding recess 1014 when assembled. When the base 806 is assembled on the inner grounding shaft 708, with locking tabs 804*a,b* extending into the notches 1016*a,b* and the proximal locking flange 1018 extending into the grounding recess 1014, the base 806 will rotate together with the inner grounding shaft 708 as described above.

Also, the slots 802*a,b* are illustrated extending longitudinally along the inner grounding shaft 708. The slots 802*a,b* are each defined or bounded by an upper surface 1020 of the inner grounding shaft 708 and a lower surface 1022 of the inner grounding shaft 708. In the illustrated example, the upper surfaces 1020 are substantially continuous along the length of the inner grounding shaft 708, but the lower surfaces 1022 are discontinuous or broken due to the grounding recesses 1012, 1014. As illustrated, the lower surfaces 1022 are absent along distal portions of the inner grounding shaft 708 corresponding with the grounding recess 1012, and the grounding recess 1014 interposes proximal portions of the lower surfaces 1022 and a distal portion of the lower surfaces 1022 extending along the locking tabs 804a,b.

The base 806, however, includes lower surfaces 1024 that define or bound portions of the slots 802a,b at locations corresponding with the grounding recesses 1012, 1014. As illustrated, the lower surfaces 1024 of the base 806 extend along the proximal locking flange 1018 of the base 806, but are discontinuous and broken via the notches 1016a,b, and then extend distally therefrom. Thus, when the base 806 is assembled on the inner grounding shaft 708, the slots 802a,b are bounded by the upper and lower surface 1020, 1022 of the inner grounding shaft 708 along proximal portions thereof and along the locking tabs 804a,b; whereas, the slots 802a,b are bounded by the upper surface 1020 of the inner grounding shaft 708 and the lower surface 1024 of the base 806 at locations along the inner grounding shaft 708 that correspond with the grounding recesses 1012, 1014.

The base 806 has an upper portion 1026 and a lower portion 1028. As illustrated, the lower surfaces 1024 define an upper surface of the lower portion 1028 of the base 806 and thereby partition the upper portion 1026 from the lower portion 1028. The base 806 also includes an articulation portion 1030 located at a distal end of the base 806. The articulation portion 1030 is configured to receive the articulation member 808 and permit rotation of the articulation member 808 relative to the base 806. As illustrated, the articulation portion 1030 includes an extension member 1032 distally extending from the upper portion 1026 of the base 806, and a pivot shaft 1034 oriented on the articulation axis $A_3$ for receiving the articulation member 808. As shown, the pivot shaft 1034 extends downward from the upper portion 1026 towards the lower portion 1028. In addition, the articulation portion 1030 includes a recess 1036 formed into the lower portion 1028 at the distal end of the base 806, which is configured to receive the articulation member 808 and permit rotation thereof within the recess 1036. As illustrated, the pivot shaft 1034 extends downward into the recess 1036 and a distal face 1038 of the lower portion 1028 includes a curvature that corresponds with a curvature of the articulation member 808, as described below.

In addition, a recess 1040 is formed into a distal end of the extension member 1032 for receiving the distal link interconnecting the drive members 720a,b as described below. The recess 1040 is defined by a sliding surface 1042 on which the distal link may slide and an upper distal face 1044 of the extension member 1032 on which the distal link may articulate or pivot, and the upper distal face 1044 may include a curvature that corresponds with a curvature of the distal link. Also in the illustrated example, a lower distal face 1046 of the extension member 1032 includes a curvature that corresponds with a curvature of the articulation member 808.

The articulation member 808 includes an end effector mounting portion 1050 at a distal end thereof and a coupling portion 1052 proximally extending from the end effector mounting portion 1050. The end effector mounting portion 1050 is configured to receive an end effector, for example, the end effector 404 of the surgical tool 400 illustrated in FIG. 4. The coupling portion 1052 is configured to be received and rotatably coupled within the recess 1036 in the distal end of the base 806, such that it may articulate relative to the base 806 when actuated by the drive members 720a,b.

The articulation member 808 includes an aperture 1054 extending through the coupling portion 1052. The aperture 1054 is configured to receive the pivot shaft 1034 of the base 806 and therefore is oriented along the articulation axis $A_3$ when the articulation member 808 is assembled on the base 806. When the base 806 and the articulation member 808 are assembled together with the pivot shaft 1034 extending through the aperture 1054, the coupling portion 1052 of the articulation member 808 is disposed within the recess 1036 defined in the lower portion 1028 the base 806 such that the articulation member 808 may rotate about the articulation axis $A_3$ relative to the base 806. Here, a proximal face 1056 of the coupling portion 1052 abuts the distal face 1038 of the base 806 and thus includes a curvature that corresponds with the curvature of the distal face 1038 of the lower portion 1028 as described above. Also, a proximal face 1058 of the end effector mounting portion 1050 abuts the lower distal face 1046 of the extension member 1032 when the articulation member 808 is assembled on the base 806. Thus, the proximal face 1058 includes a curvature that corresponds with the curvature of the lower distal face 1046 of the extension member 1032 and, in some examples, the curvature of the proximal face 1058 is defined by a radius equal to the swept distance that the extension member 1032 extends beyond the articulation axis $A_3$ (i.e., distance between the articulation axis $A_3$ and the lower distal face 1046).

The articulation member 808 includes a pair of drive pins 1060a,b configured to be engaged by the drive members 720a,b. Here, the drive pins 1060a,b extend upward from an upper surface 1062 of the coupling portion 1052. When the base 806 and the articulation member 808 are assembled together, with the coupling portion 1052 rotatably disposed within the recess 1036 and with the pivot shaft 1034 extending through the aperture 1054, the upper surface 1062 of the coupling portion 1052 is substantially aligned or planar with the lower surfaces 1024 of the base 806 such that the drive members 720a,b may slide unobstructed thereon. Also, the drive pins 1060a,b extend upward from the upper surface 1062 of the coupling portion 1052 a sufficient distance such that they may be engaged by the drive members 720a,b when riding in the slots 802a,b.

In the illustrated example, the drive pins 1060a,b extend upward from the upper surface 1062 and each terminate at a pin end 1064a,b. Here, the pin ends 1064a,b are cylindrical members extending upward from the drive pins 1060a,b and have a reduced diameter from the drive pins 1060a,b from which they coaxially extend. The pin ends 1064a,b each define a surface 1066 that is substantially aligned or planar with an upper surface 1068 of the base 806 extending onto the extension member 1032 thereof. Thus, when the base 806 and the articulation member 808 are assembled together, the drive pins 1060a,b extend upward from the sliding surface 1042 and the pin ends 1064a,b extend upward from the drive pins 1060a,b such that the surfaces 1066 of the pin ends 1064a,b are oriented parallel with the upper surface 1068 of the base 806. In other examples, however, the drive pins 1060a,b and/or the pin ends 1064a,b may extend upward at different heights, and in some examples the drive pins 1060a,b do not include pin ends 1064a,b such that the drive pins 1060a,b are cylinder shaped members having a uniform diameter.

FIG. 10B also illustrates the drive members 720a,b, each of which provides a distal end 1070a and 1070b, respectively, configured to engage the articulation member 808. A drive pin aperture 1072 is provided at the distal end 1070a,b of each drive member 720a,b and is configured to receive the drive pins 1060a,b of the articulation member 808 when the articulation member 808 is assembled on the base 806 and to allow the drive pins 1060a,b to translate laterally within the corresponding aperture 1072 when the drive members 720a,b are actuated to articulate the wrist 406. The drive pin apertures 1072 may have various geometries, for example, rectangular or square shape geometries. In the illustrated example, the drive pin apertures 1072 have a generally rectangular shape with rounded corners, which allows relative translation of the drive pins 1060a,b during articulation. Regardless of their shape, the drive pin apertures 1072 are sized to receive the drive pins 1060a,b or at least a portion of the drive pins 1060a,b.

Also, the distal ends 1070a,b of the drive members 720a,b are constrained together via a distal link 1074. As mentioned above, the drive members 720a,b and the distal link 1074 together comprise a linkage that articulates the articulation member 808. The distal link 1074 includes a pair of wings 1076a and 1076b that correspond with the distal ends 1070a,b of the drive members 720a,b, and each wing 1076a,b includes an aperture 1078 configured to receive one of the drive pins 1060a,b or a portion thereof. In the illustrated example, the apertures 1078 are circular shaped holes configured to receive the pin ends 1064a,b of the drive pins 1060a,b. In examples where the drive pins 1060a,b do not include reduced diameter pin ends 1064a,b, the apertures 1078 may be circular shaped holes sized to receive the drive pins 1060a,b. The apertures 1078 may have various other shapes, however. In some examples, the apertures 1078 are shaped to correspond with the drive pin apertures 1072 of the drive members 720a,b. In addition, the distal link 1074 includes a bridge portion 1080 interconnecting the wings 1076a,b, and the bridge portion 1080 includes an interior pivot surface 1082 configured to engage and pivot on the upper distal face 1044 of the extension member 1032 (of the base 806). Here, the pivot surface 1082 includes a curvature that corresponds with the curvature of the upper distal face 1044.

When assembled, the drive pins 1060a,b couple the drive members 720a,b to the distal link 1074. For example, the drive members 720a,b extend distally in the slots 802a,b along the lower surfaces 1022,1024 and the distal ends 1070a,b extend over the coupling portion 1052 of the articulation member 808, with the lower portions of the drive pins 1060a,b extending upward into the apertures 1072 in the drive members 720a,b. Also, the distal link 1074 is arranged in the recess 1042 of the base 806, with the bridge portion 1080 disposed on the sliding surface 1042 and the pivot surface 1082 abutting the upper distal face 1044, such that the pin ends 1064a,b of the drive pins 1060a,b extend upward through the apertures 1078 of the distal link 1074. Translation of the drive members 720a,b pushes and pulls on the drive pins 1060a,b of the articulation member 808, thereby rotating the articulation member 808 about the articulation axis $A_3$. Thus, the articulation member 808 may be rotated about the articulation axis $A_3$, which thereby articulates the wrist 406, via activation of the drivers 610b,c (FIG. 6) that engage the drive inputs 608b,c (FIG. 6).

Referring again to FIGS. 7A and 7B, a sixth drive shaft 702f is coupled to the sixth drive input 608f (FIG. 6) such that actuation and rotation of the sixth drive input 608f correspondingly rotates the sixth drive shaft 702f. Rotating the sixth drive shaft 702f may advance and retract a firing rod (not shown) that extends through the shaft 402 to the end effector 404 (FIG. 4). The distal end of the firing rod is operatively coupled to the cutting element (knife) such that axial movement of the firing rod correspondingly moves the cutting element distally or proximally to transect tissue grasped between the jaws 410, 412 (FIG. 4). In some embodiments, distal movement of the firing rod also deploys the staples, as described above.

A spur gear 730 is coupled to the sixth drive shaft 702f such that rotation of the sixth drive shaft 702f correspondingly rotates the spur gear 730. The spur gear 730 intermeshes with a second spur gear 732, which is attached to a first transfer drive shaft 734. A third spur gear (not visible) is coupled to the first transfer drive shaft 734 and intermeshes with a fourth spur gear 736, which is attached to a second transfer drive shaft 738. Finally, an output pinion gear 740 (FIG. 7A) is coupled to the second transfer drive shaft 738 and intermeshes with a rack gear 742 of a firing member 744 such that rotation of the output pinion gear 740 causes axial translation of the firing member 744. The firing member 744 may be coupled to the firing rod (not shown) discussed above. Accordingly, rotation of the sixth drive shaft 702f will drive the firing member 744 in axial translation, which correspondingly drives the firing rod in the same direction to advance and retract the cutting element at the end effector 404 (FIG. 4).

As described above, the tool driver 604 (FIG. 6) includes one or more drivers 610a-f (FIG. 6) configured to actuate corresponding drive inputs 608a-f (FIG. 6), and each driver 610a-f may be powered by a corresponding motor 616 (FIG. 6). Mating engagement between the drivers 610a-f and the corresponding drive inputs 608a-f allow the drivers 610a-f to be activated to impart rotation to the corresponding drive shafts 702a-f extending from the drive inputs 608a-f. As mentioned, the wrist 406 is articulated by driving the second and third drive inputs 608b,c, which may be individually driven, one at a time, via the second and third drivers 610b,c. To increase available torque, however, the drive inputs 608b,c may be antagonistically driven by both drivers 610b,c at the same time.

While controlling articulation of the wrist 406 with the drivers 610b,c increases potential torque to accomplish a desired articulation of the wrist 406, simultaneously operating the drivers 610b,c presents potential for over-constrained mechanisms, thereby impairing operation of the surgical tool 400. Thus, the robotic surgical system 100 may include the computer system 600 (FIG. 6) configured to control and synchronize operation of the drivers 610b,c (or any two or more of the drivers 610a-f of FIG. 6) such that they operate as a single input (i.e., function as a single driver) more efficiently. This may help prevent over-constraining drive components coupled thereto, such as the drive inputs 608b,c (FIG. 6), the drive shafts 702b,c (FIGS. 7A-7B), the articulation yokes 716a,b (FIGS. 7A-7B), etc.

Figure 11A:
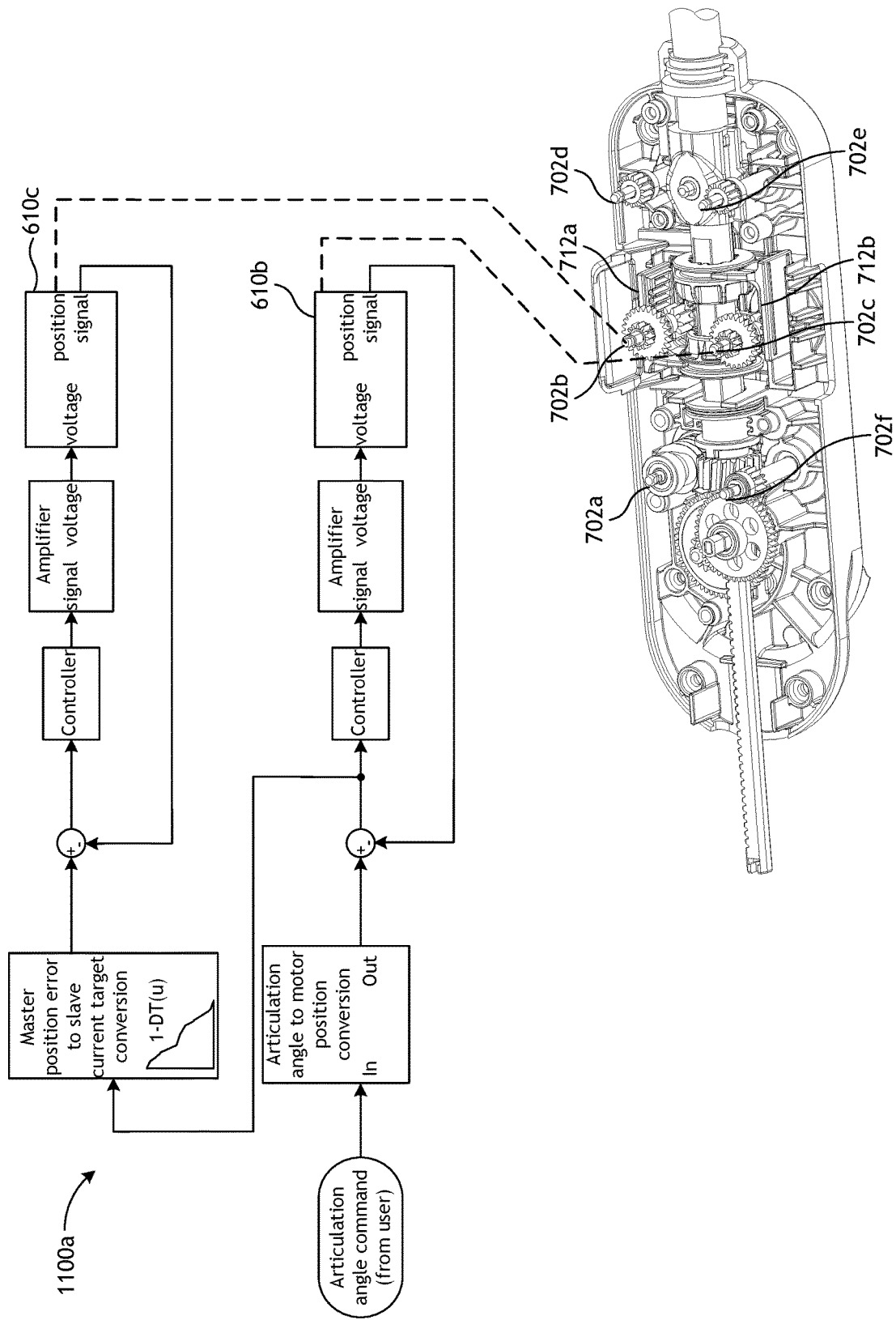
FIGS. 11A-11C illustrate various example algorithms programmable into the computer system of FIG. 6 to control operation of the drivers of FIG. 6, according to various embodiments of the present disclosure.
Figure 11B:
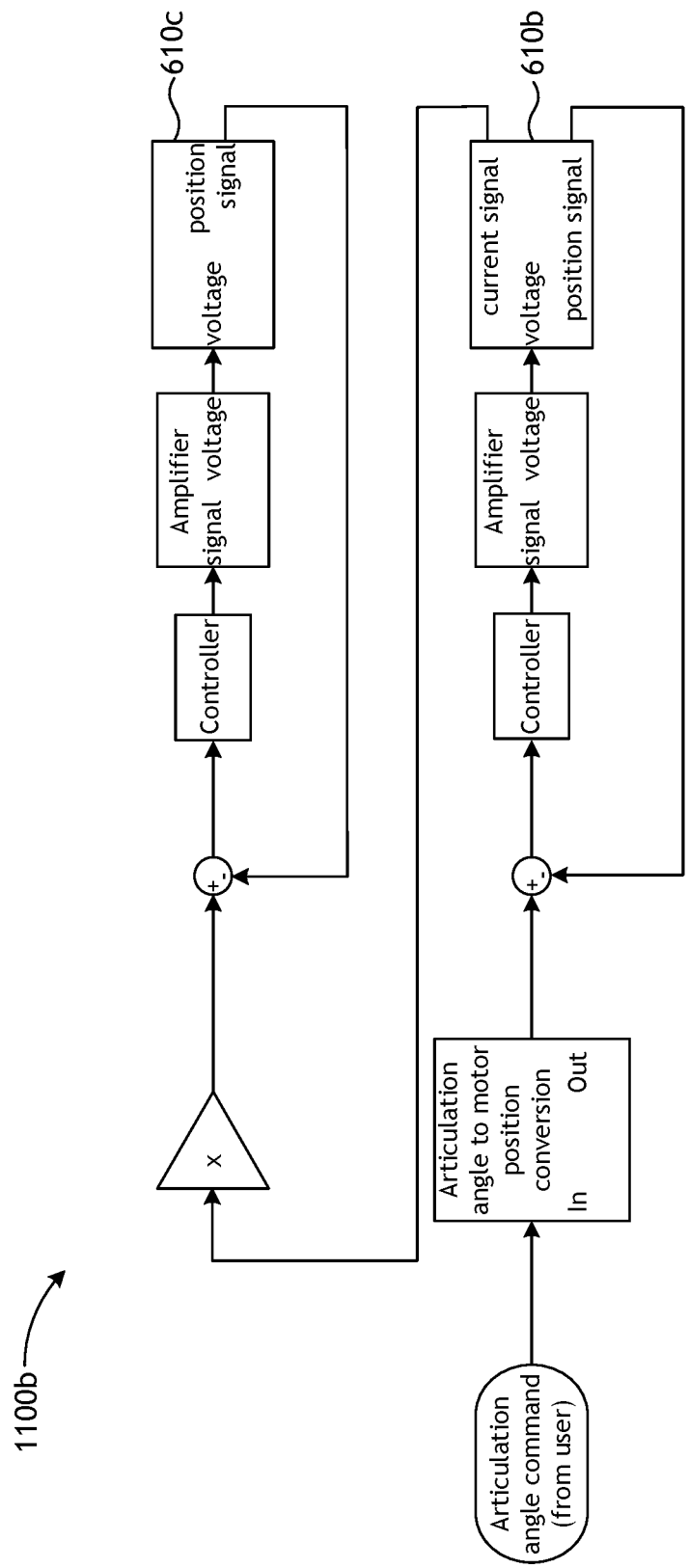
Figure 11C:
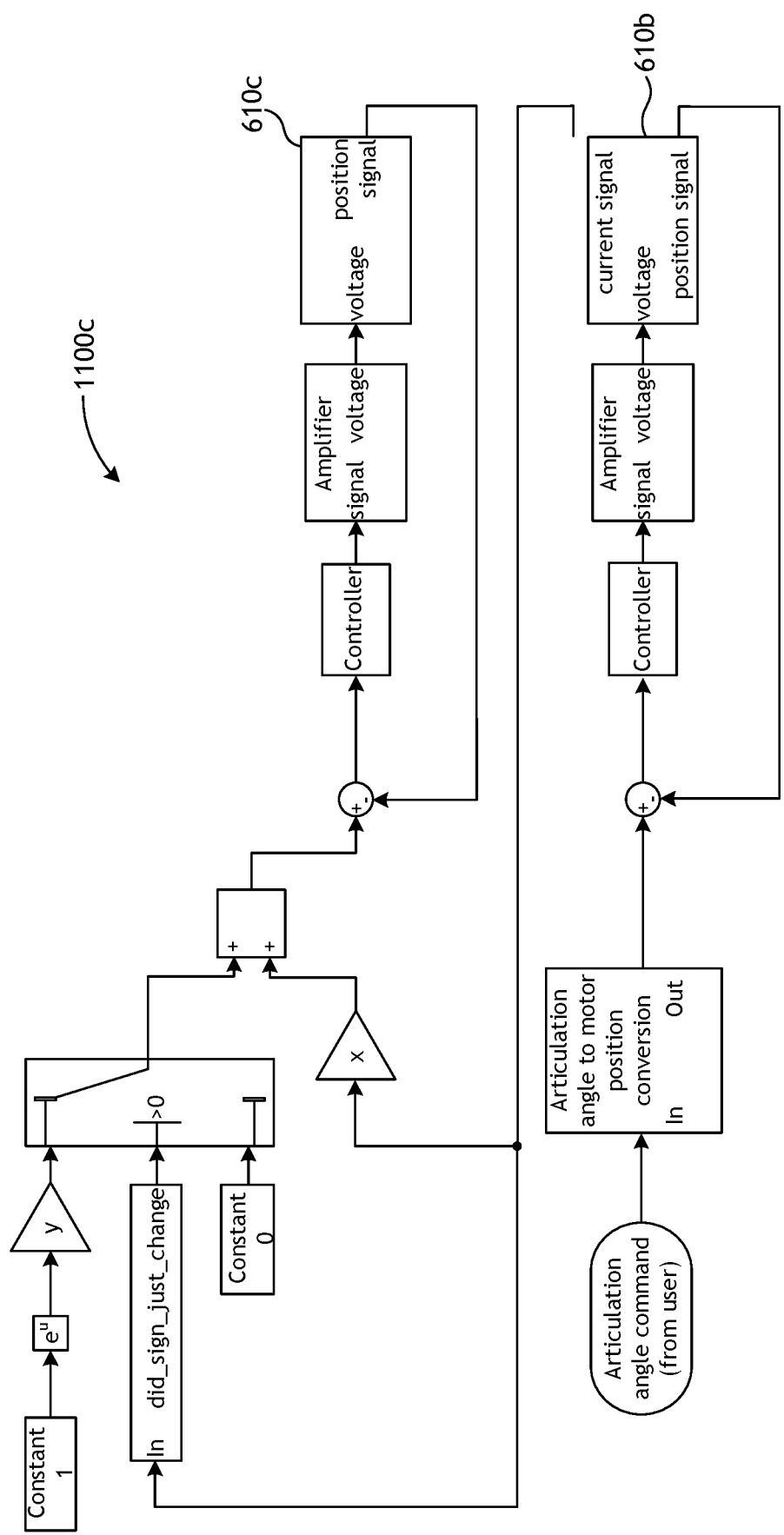

FIGS. 11A-11C illustrate various example algorithms programmable into the computer system 600 of FIG. 6 to control operation of the second and third drivers 610b,c (FIG. 6), according to various embodiments of the present disclosure. Each algorithm identifies and operates a "master motor," corresponding to one of the drivers 610b,c, and a "slave motor," corresponding to the other of the drivers 610b,c. As discussed above, the second and third drivers 610b,c are operatively coupled to the drive inputs 608b,c (FIG. 6) to cause rotation of the corresponding drive shafts 702b,c. The algorithms described herein may comprise software code instructions programmed into the computer system 600 to help prevent mechanical binding of the internal drive mechanisms within the drive housing 408 that are coupled to the drivers 610b,c.

It should be noted that while the example algorithms are described herein with respect to operation of the drivers 610b,c to cause rotation of the drive shafts 702b,c, one or more of the algorithms may be utilized with respect to any other of the drivers 610a-f (FIG. 6). For example, one or more of the algorithms may alternatively (or in addition thereto) be configured to control the fifth and sixth drivers 610e,f operatively coupled to the fifth and sixth drive shafts 702e,d to cause clamping of the jaws 410, 412 (FIG. 4).

In FIG. 11A, a first algorithm 1100a may be configured to control the position of the "master motor" using feedback to achieve a device target set by the clinician 112a. More specifically, the first algorithm 1100a may be configured to directly control the slave current based on the master current. Here, the target slave current is equal to the actual master current output to the "master motor." In the illustrated example, the second driver 610b is designated as the "master motor" and the third driver 610c is designated as the "slave motor." The clinician 112a may pinch or manipulate the user input device 203 to effect articulation of the wrist 406 into a desired orientation or wrist angle. Thus, the clinician 112 inputs a desired orientation or wrist angle for the wrist 406 into the computer system 600 (FIG. 6) via manipulation of the user input device 203. Similarly, the clinician 112a may pinch or manipulate the user input device 203 to effect movement of either or both of the jaws 410, 412 (FIG. 4) into a desired orientation or closure angle, and thereby input a desired orientation or closure angle for the jaws 410, 412 into the computer system 606. By applying the algorithm 1100a, the computer system 606 then converts the desired orientation or wrist angle of the wrist 406 (and/or the desired orientation or closure angle of the jaws 410, 412, the end-effector 404 position target, etc.) into a master motor position target using a formula for the mechanism moving or positioning the wrist 406 (and/or the jaws 410, 412, etc.). In one example, the formulae are:

$$R3 = GearRatio * \left(\frac{180}{\pi}\right) * pinRadius * \frac{\sin\left(articulationAngleCommanded * \frac{\pi}{180}\right)}{gearRadius}$$

$$R4 = GearRatio * \left(\frac{180}{\pi}\right) * pinRadius * \frac{\sin\left(articulationAngleCommanded * \frac{\pi}{180}\right)}{gearRadius}$$

In these formulae, the "pinRadius" is the distance between a central axis of the pivot shaft 1034 (of the base 806) and the central axis of one of the pins 1060a,1060b (of the articulation member 808) as evaluated in a plane in which the wrist 406 articulates, wherein "gearRadius" is the radius of the second pinion gear 713a,713b of the compound pinion gear 710a,710b, and the "GearRatio" is of the combined gear ratio of the spur gear 709a,709b, the idler assembly 715a,715b, and the first pinion gear 711a,711b.

Via the algorithm 1100a, the computer system 606 (FIG. 6) may continuously monitor the actual position (e.g., angular position) of the "master motor" relative to the master motor position target, and then subtracts a master motor actual position from the master motor target position to yield a master position error. Based on the algorithm 1100a, the computer system 606 may then supply voltage to the "master motor" through a master or primary control loop depending on the master position error, a change in the master position error, and/or an accumulation of the master position error over time. Meanwhile, the master position error of the master control loop is fed to a secondary or slave control loop for the "slave motor."

In some embodiments, the algorithm 1100a may utilize a lookup table to convert the master position error into a slave motor target current, and a feedback controller of the slave control loop monitors a slave motor actual current and modulates voltage supplied to the "slave motor" to achieve the slave motor target current. In doing so, the "master motor" works to achieve the target motor position (corresponding with the desired orientation or wrist angle of the wrist 406 and/or desired closure angle of the jaws 410, 412), with the "slave motor" operating in concert by helping push or pull internal drive components in the same direction as urged by the "master motor" rather than acting against or pushing such internal drive components in an opposite direction from that urged by the "master motor." For example, as the second driver 610b causes rotation of the drive shaft 702b to distally translate the first drive member 720a and thereby articulate the wrist 406, the third driver 610c will assist achieving such desired articulation by causing the third drive shaft 702c to rotate and thereby move the second drive member 720b proximally. Thus, both the drivers 610b,c may work in concert to complementarily cause articulation of the wrist 406 (i.e., protagonistically), rather than just one of the drivers 610b,c operating independently with one of the drivers 610b,c possibly off-setting the force output by the other (i.e., antagonistically).

FIG. 11B is a schematic diagram of another algorithm 1100b that may be programmed into the computer system 606 of FIG. 6. The second algorithm 1100b may be configured to control the slave current based on a proportion of the master current. Here, the target slave current is equal to a proportion of the actual master current output to the "master motor."

FIG. 11C is a schematic diagram of a third algorithm 1100c that may be programmed into the computer system 606 of FIG. 6. The third algorithm 1100c may be configured to control the slave current based on both a proportion of the master current and direction changes sensed in the "master motor." More specifically, the "master motor" direction changes are sensed as the master current changes between a positive or negative values (and vice versa), and each such direction change generates a decaying current spike that is added to the proportion of the actual master current output to the "master motor." Using exponentially decaying current spikes generated after each direction change of the "master motor," in addition to the proportional master current, helps the "slave motor" catch up to the "master motor."

As described herein, the drivers 610a-f of FIG. 6 are configured to mate with corresponding drive inputs 608a-f (FIG. 6) to cause rotation of associated drive shafts 702a-f (FIGS. 7A-7B) connected thereto, which results in various movements of the end effector 404 (FIG. 4) and/or the wrist 406 (FIG. 4). Each drive input 608a-f may have a neutral or unarticulated position where they do not impart a corresponding movement to the end effector 404 and/or the wrist 406, but the drive inputs 608a-f can sometimes be moved from the neutral position before the tool 400 is coupled to the tool driver 604 (FIG. 6). In some cases, for example, the drive inputs 608a-f may have been previously actuated out of their neutral positions to cause movement in the end effector 404 and/or the wrist 406 during prior use. In other cases, or in addition thereto, one or more of the drive inputs 608a-f may be rotated out of their neutral positions during sterilization or cleaning.

However, it is important to be able to quickly and accurately return the drive inputs 608a-f to the neutral positions during or prior to use. In order to ensure that the drivers 610a-f do not command the drive inputs 608a-f to positions that may cause damage to the surgical tool 400, systems may be provided for accurately "homing" the surgical tool 400 or one or more sub-systems of the surgical tool 400. For example, the drive inputs 608a-f may have home positions corresponding with known positions of the end effector 404 and/or the wrist 406, and homing the surgical tool 400 may relate the angular position of the drivers 610a-f and, by extension the drive inputs 608a-f coupled thereto, to the known positions of the end effector 404 and/or the wrist 406. Not only may this relationship be utilized to inhibit over-actuation (or over-rotation) of the drive inputs 608a-f that may otherwise cause damage to the surgical tool 400, but this relationship may be utilized to establish the actual position the end effector 404 and/or the wrist 406 in space.

Conventional homing systems often utilize mechanical limit switches and closely monitor torque output by the drivers 610a-f to find the home position for the drive inputs 608a-f. To do this however, the drivers 610a-f must be rotated slowly so as to be able to detect torque spikes prior to hitting a hard stop and potentially breaking components associated with the limit switches. This can add a significant amount of time to a homing sequence, especially when utilizing surgical tools having high gear ratios.

According to embodiments of the present disclosure, the robotic surgical system 100 (FIG. 1) may include a homing system configured to quickly return (or home) the drive inputs 608a-f to their neutral positions. The surgical tool 400 (FIG. 4) may be manufactured to be installed on the sterile barrier of the robotic manipulator so that the rotational position of the drive inputs 608a-f are known. For example, the drive inputs 608a-f may each be keyed to couple to their corresponding driver 610a-f when in a certain rotational position. This permits the homing system to identify the relative rotational (angular) position of the drive inputs 608a-f when the surgical tool 400 is coupled to the tool driver 604 (FIG. 6) and associate that relative rotational position of the drive inputs 608a-f with a specific cumulative motor position of the driver 610a-f that is known by the homing system.

During manufacture, the surgical tool 400 is calibrated to determine the absolute rotational value at which each of the drive inputs 608a-f is in its home position (e.g., 180°), and these known calibrated home positions are stored in a memory of the surgical tool 400 and accessible by the surgical system 100 when the surgical tool 400 is coupled to the tool driver 604 (FIG. 6). A window or "slow zone," which is a range of rotational positions surrounding the known calibrated home positions at which the drive inputs 608a-f may be in the home position (e.g., 180°±40°), may be built around the known calibrated home positions and similarly stored in a memory of the surgical tool 400 (e.g. the computer system 606 of FIG. 6). The homing system may communicate with the rotary encoders 630 (FIG. 6) to determine the angular and/or rotational position of each drive input 608a-f. When the drive inputs 608a-f are being rotated near the corresponding "slow zones" based on the absolute motor position of the drivers 610a-f as measured by the corresponding rotary encoders 630, the homing system may be programmed to decrease the speed at which the drivers 610a-f rotate the drive inputs 608a-f.

Figure 12:
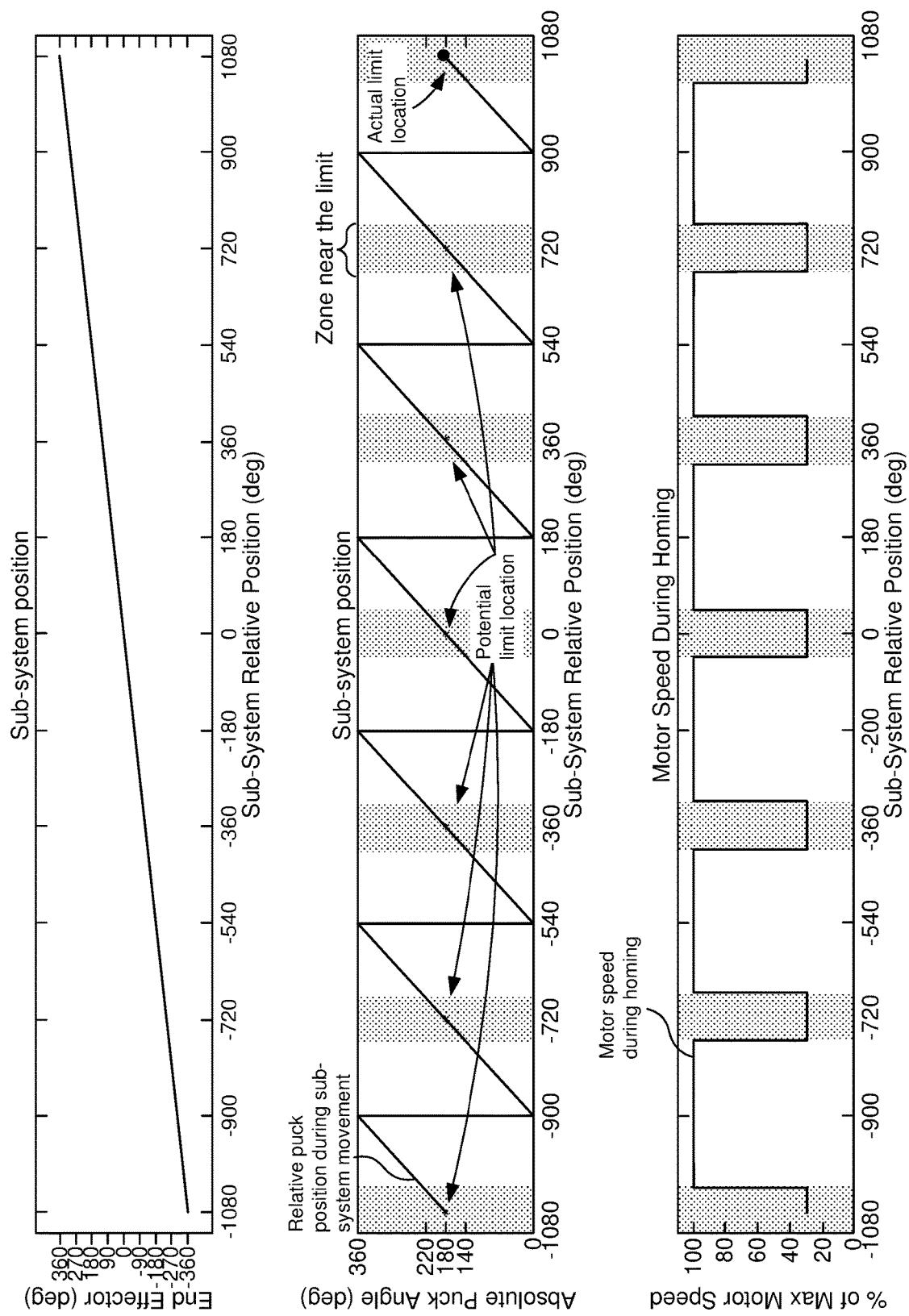
FIG. 12 illustrates a set of graphs showing an example operation of an example homing system, according to one or more embodiments of the disclosure.

FIG. 12 illustrates top, middle, and bottom graphs that illustrate operation of an example homing system configured to intelligently adjust the homing speed of the surgical tool 400 (FIG. 4) based on the rotational position of the drivers 610a-f and/or the drive inputs 608a-f operatively coupled thereto, according to one or more embodiments. In the illustrated example, the surgical tool 400 was manufactured such that the home position of one of the drive inputs 608a-f occurs at an absolute angular position of 180° and the surgical tool 400 was calibrated to determine that the drive input 608a-f may be rotated (clockwise or counter-clockwise) six (6) full revolutions from that home position until a limit is reached. The neutral position of the drive input 608a-f is located at the midpoint of the total range. Positions of the sub-system before the neutral position will be negative; whereas, positions of the sub-system after the neutral position will be positive. The surgical tool 400 in this example has a gear ratio such that three (3) rotations of one of the drive inputs 608a-f results in one (1) rotation of the end effector 404. This information may be stored in the surgical tool 400, such as in the computer system 606 (FIG. 6) or the memory 624 (FIG. 6) of the internal computer 622 (FIG. 6). Mating the drive housing 408 to the tool driver 604 places the internal computer 622 in communication with the computer system 606. Also, a "slow zone" of 80° was designed to encompass that absolute angular position of the drive input 608a-f, thereby providing a buffer of 40° ranging before and after the absolute angular position of 180° (e.g., 180°±40°) which may correspond with the drive input 608a-f being in a home position, and this information was also stored in the surgical tool 400.

In FIG. 12, the top graph illustrates the angular position of the end effector 404 in degrees versus the relative sub-system position in degrees. The surgical tool 400 in this example begins the homing procedure in the maximum six (6) full revolutions from the home position. This graph shows that the sub-system starts at the negative extreme of its position, moves towards the neutral position, and continues in that direction until reaching its positive extreme.

The middle graph in FIG. 12 illustrates the absolute angular measurement of the rotational position of one of the drive inputs 608a-f in degrees versus the relative sub-system position in degrees. This graph illustrates the absolute angular position of one of the drive inputs 608a-f returning to 0° after reaching 360° because it shows the absolute position, rather than incremental position, of the drive inputs 608a-f. This graph also illustrates the potential neutral position occurring at an absolute angular position of 180° that is keyed to a known relative sub-system position, and how the drivers 610a-f may rotate the drive inputs 608a-f six (6) full revolutions until the actual neutral position is reached. Moreover, this graph shows the "slow zone" of 80° built around the absolute angular position of one of the drive inputs 608a-f, and how the "slow zones" are keyed to a known cumulative position of the driver 610a-f.

The bottom graph in FIG. 12 illustrates how the homing system may adjust the speed at which the drivers 610a-f drive the drive inputs 608a-f based on the relative sub-system position in degrees. Here, the bottom graph illustrates the drivers 610a-f rotating the drive inputs 608a-f at a first speed when the drive inputs 608a-f are not rotationally oriented within the "slow zones" and then stepping down the speed to a second speed that is less than the first speed when the drive inputs 608a-f are rotationally oriented within the "slow zones."

Figure 13:
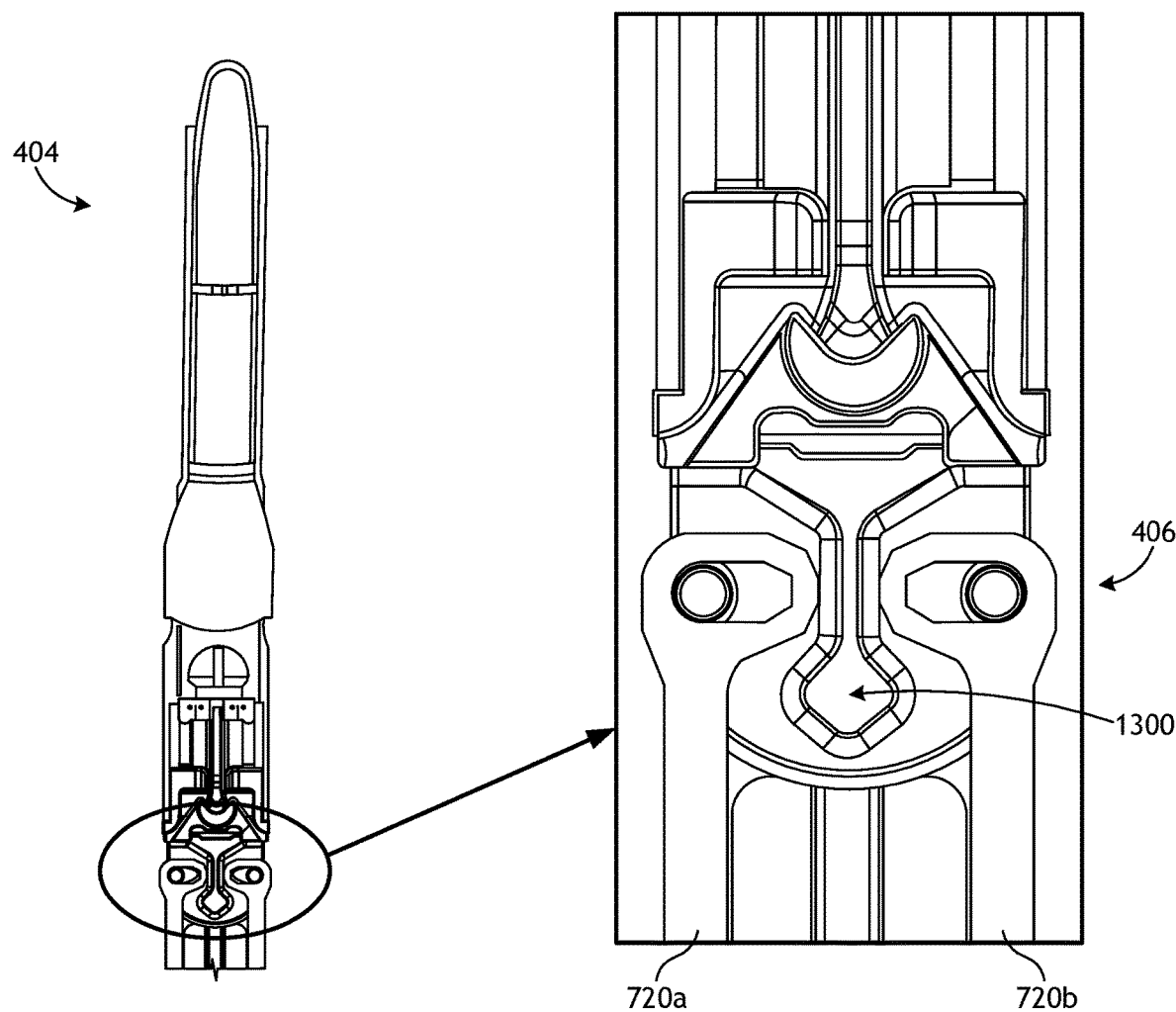
FIG. 13 illustrates to exposed view of an exemplary joint of the wrist in FIGS. 10A-10B.

FIG. 13 illustrates an articulating joint 1300 for helping facilitate articulation of the wrist 406, according to one or more embodiments of the present disclosure. As described above, the wrist 406 may be articulated within a plane by antagonistically actuating a linkage assembly. More specifically, the wrist 406 may be rotated clockwise by pushing the first drive member 720a while simultaneously pulling the second drive member 720b, and the wrist 406 may be rotated counter-clockwise by pulling the first drive member 720a while simultaneously pushing the second drive member 720b. Accordingly, the joint 1300 may be rotated via antagonistic translation of the first and second drive members 720a,b and, as previously described, the drive members 720a,b are actuated by operation of the second and third drive inputs 608b,c (FIG. 4), respectively, which in turn are driven by the second and third drivers 610b,c (FIG. 4), respectively.

During a surgical procedure, however, the end effector 404 and the wrist 406 may be disposed within a body cavity and potentially abutting patient tissue. In such cases, the articulating joint 1300 may potentially need to move adjacent tissue. Thus, to move the wrist 406 into a desired orientation, the robotic surgical system 100 may be configured such that the second and third drivers 610b,c (FIG. 4) cause the drive members 720a,b to translate with force sufficient to overcome any external load applied by tissue during a procedure, and to hold or maintain that desired orientation even when subjected to such an external load.

Figure 14:
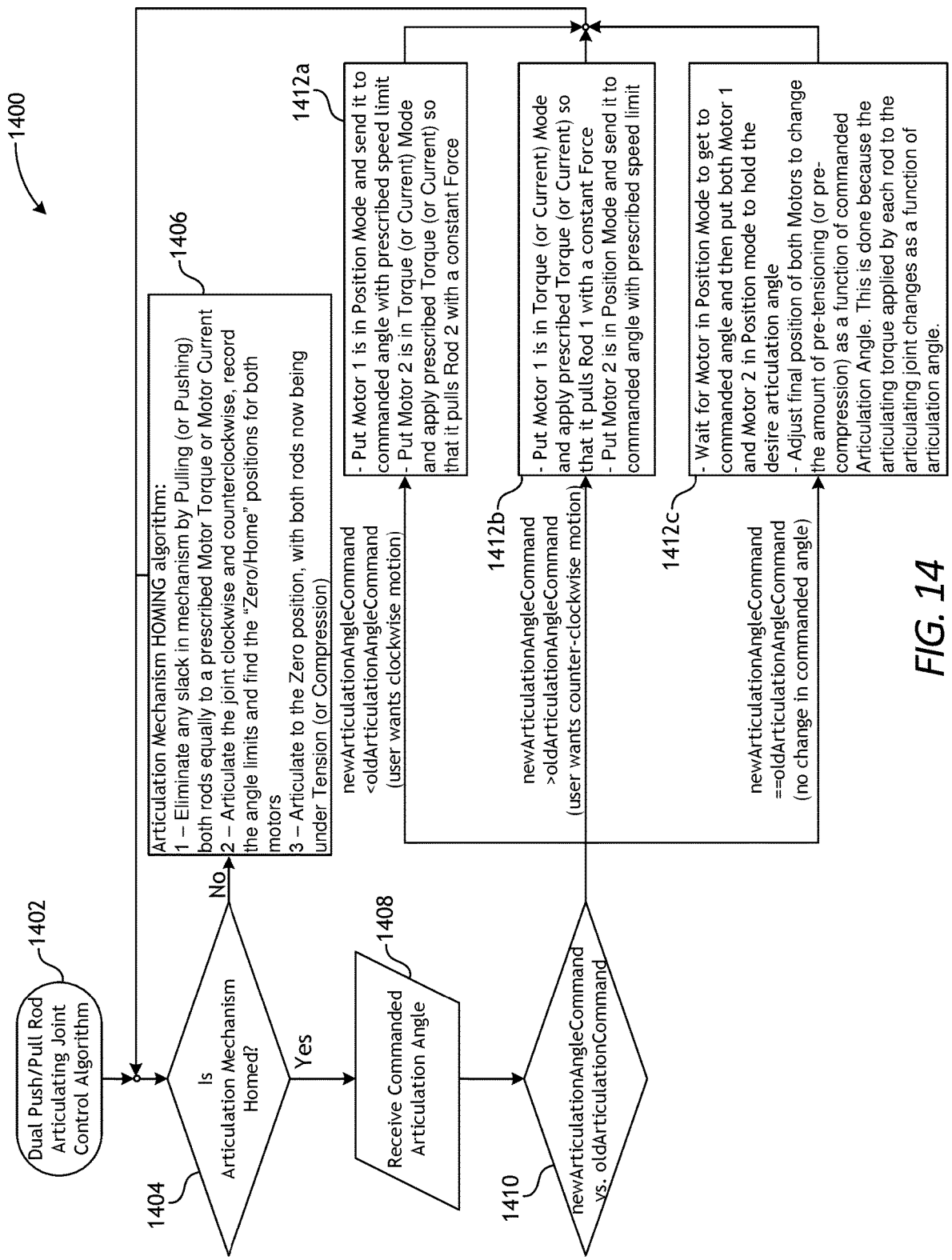
FIG. 14 is a schematic of an exemplary method for controlling articulation of the joint of FIG. 13, according to one or more embodiments of the disclosure.

FIG. 14 is a schematic diagram of an example control scheme 1400 that may be used to control articulation of the wrist 406 via the joint 1300 of FIG. 13, according to one or more embodiments. In the illustrated example, the control scheme 1400 utilizes an algorithm that allows for smooth and continuous articulation of the articulation joint 1300, locks the articulation joint 1300 so that it is cannot be moved by an external load, and actively works against any external load as the articulation joint 1300 is being articulated into a desired angle.

In the illustrated example, the control scheme 1400 begins at a starting point 1402. The control scheme 1400 first determines whether the mechanism articulating the joint 1300 is properly homed, as at node 1404. If the joint 1300 is not properly homed, the control scheme 1400 initiates a homing sequence or homing process, as at 1406. During the homing process of 1406, the joint 1300 is homed by eliminating any slack in the joint 1300 mechanism by antagonistically articulating (i.e., pulling and pushing, respectively) the drive members 720a,b equally to a prescribed torque or current for the corresponding driver 610b,c; articulating the joint 1300 (clockwise or counter-clockwise) and recording the angle limits to find the home positions for both drivers 610b,c; and articulating the joint 1300 to where the drivers 610b,c are in their home positions with the drive members 720a,b being under tension and compression, respectively.

If the joint 1300 is properly homed, the clinician 112a can direct or command the robot to articulate the joint 1300 to a desired articulation angle. More specifically, if the control scheme 1400 determines that the mechanism of the joint 1300 is properly homed, an articulation command input may be provided to the control scheme 1400, as at 1408. The articulation command input may be indicative of the articulation angle of the joint 1300 desired by the clinician 112a. The control scheme 1400 proceeds by comparing a new articulation command of the joint 1300 (i.e., "newArticulationAngleCommand") to an old articulation command of the joint 1300 (i.e., "oldArticulationCommand", as at 1410. Here, the control scheme 1400 may determine whether the new articulation command of the joint 1300 is less than, greater than, or equal to the old articulation command of the joint 1300. Depending on the relative values of the new and old articulation commands, the control scheme 1400 initiates a separate articulation process, depicted herein as articulation processes 1412a, 1412b, and 1412c.

Also, the relative values of the new and old articulation commands are indicative of whether the clinician 112a wants to move the wrist 406 or not. For example, the clinician 112a may want to articulate the joint 1300 in a clockwise motion or in a counter-clockwise motion or maintain the joint 1300 in a particular position. If the clinician 112a commands the joint 1300 to articulate the wrist 406 in a clockwise motion, the control scheme 1400 initiates the first articulation process, as at 1412a. If the clinician 112a commands the joint 1300 to articulate the wrist 406 in a counter-clockwise motion, the control scheme 1400 initiates the second articulation process, as at 1412b. If the clinician 112a does not command the joint 1300 to articulate the wrist 406, meaning the wrist 406 is to maintain its position, the control scheme 1400 initiates the third articulation process, as at 1412c.

In the illustrated example, the control scheme 1400 initiates the first articulation process 1412a if it determines at the decision node 1410 that the new articulation command is less than the old articulation command, meaning that the joint 1300 is to move clockwise. Here, the first articulation process 1412a puts the second driver 610b associated with the first drive member 720a in its position mode and actuates the third driver 610c into a commanded angle at a prescribed speed limit, and the first articulation process 1412a simultaneously puts the third driver 610c associated with the second drive member 720b in torque (or current) mode to apply a prescribed torque (or current) to the third driver 610c so that it pulls the second drive member 720b with a constant force.

In the illustrated example, the control scheme 1400 initiates the second articulation process 1412b if it determines at the decision node 1410 that the new articulation command is greater than the old articulation command, meaning that the joint 1300 is to move counter-clockwise. Here, the second articulation process 1412b puts the second driver 610b associated with the first drive member 720a in torque (or current) mode to apply a prescribed torque (or current) to the second driver 610b so that it pulls the first drive member 720a with a constant force, and the second articulation process 1412b simultaneously puts the third driver 610c in its position mode and actuates the third driver 610c into a commanded angle at a prescribed speed limit.

In the illustrated example, the control scheme 1400 initiates the third articulation process 1412c if it determines at the decision node 1410 that the new articulation command equal to the old articulation command, meaning that there is no change in articulation command is the joint 1300 is to remain stationary. Here, the third articulation process 1412c waits for whichever of the second or third drivers 610b,c that is in position mode to move into its commanded angle and then puts both the second and third drivers 610b,c into position mode to hold or maintain the joint 1300 at that position which corresponds with the desired articulation angle of the wrist 406.

In addition, the third articulation process 1412c may adjust the final commanded angles or position of one of the second or third driver 610b,c that follows movement of the other of the second or third driver 610b,c, so that the final pre-tensioning in the drive members 720a,b would be equal to the original pre-tensioning in the drive members 720a,b, as the amount of torque applied by each of the drive members 720a,b to the joint 1300 varies depending on the angle of the joint 1300. In particular, say the wrist 406 of the articulation sub-system is initially homed by moving the second and third drivers 610b,c, so that there is a certain amount of pre-tensioning in the drive members 720a,b, and then the second driver 610b is moved in response to a new articulation command input by the clinician 112a. As the second driver 610b is moved, thereby pulling the drive member 720a corresponding therewith, the other motor (i.e., the third driver 610c) may either be disabled (i.e., goes limp) or be put in current mode with minimal current applied to it. Here, as the second driver 610b is moved to achieve its final destination where the joint 1300 is moved into an angular position corresponding with the articulation command, the third driver 610c is put into position mode and is set to a target position, and the target position is changed as a function of the articulation command so that the tensioning of the drive members 720a,b would equal the amount of pre-tensioning initially applied to the drive members 720a,b. Thus, the angular distance between the second and third drivers 610b,c may change as a function of the articulation angle of the joint 1300. For example, if the second and third drivers 610b,c are fifty degrees (50°) apart initially to have a pre-tensioning torque of 0.1 Nm, and then the joint 1300 is articulated to an angle of ten degrees (10°), the second and third drivers 610b,c would be moved so that they're sixty degrees (60°) apart to have equal pre-tensioning in the drive members 720a,b.

Figure 15A:
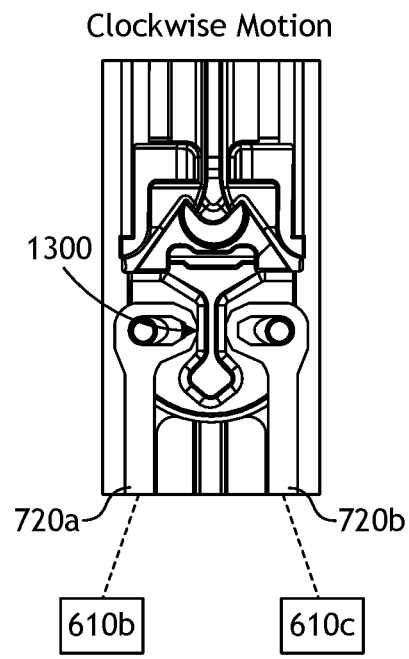
FIGS. 15A and 15B are top exposed views of the wrist of FIG. 13 illustrating example operation of the method of FIG. 14.
Figure 15B:
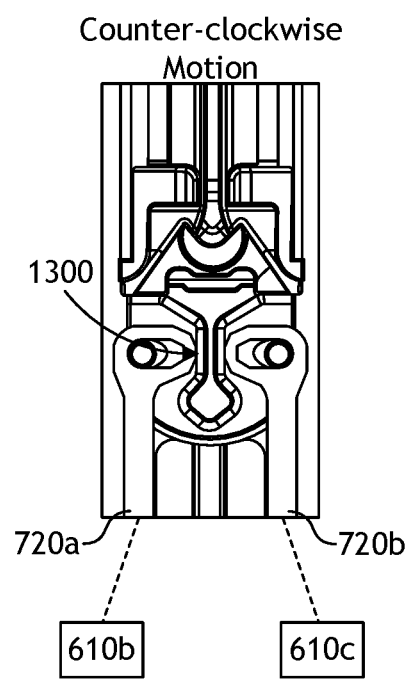

FIGS. 15A and 15B illustrate example operation of the control scheme 1400 of FIG. 14. In particular, FIG. 15A illustrates application of the first articulation process 1412a in controlling the drivers 610b,c to articulate the joint 1300 in a clockwise direction, and FIG. 15B illustrates application of the second articulation process 1412b in controlling the drivers 610b,c to articulate the joint 1300 in a counter-clockwise direction. In FIG. 15A, the control scheme 1400 has placed the second driver 610b in position mode, where the control scheme 1400 polices (monitors) motion of the second driver 610b that translates the first drive member 720a, and where the control scheme 1400 allows the third driver 610c that controls the second drive member 720b to pull at a limited motor torque. In addition, the control scheme 1400 has placed the third driver 610c in torque (or current) mode where the third driver 610c applies constant pulling (or pushing) to force to the second drive member 720b.

In FIG. 15B, the control scheme 1400 has placed the third driver 610c in position mode, where the control scheme 1400 polices (monitors) motion of the third driver 610c that causes translation (movement) of the second drive member 720b, and where the control scheme 1400 allows the second driver 610b that controls the first drive member 720a to pull at a limited motor speed. In addition, the control scheme 1400 has placed the second driver 610b in torque (or current) mode where the second driver 610b applies constant pulling (or pushing) to force to the first drive member 720a.

It is often desirable to articulate the joint 1300 as quickly as possible to thereby enhance responsiveness of the surgical tool 400 (FIG. 4). However, there are physical limits to the amount that the joint 1300 may articulate and, when articulating the joint 1300 at high speeds, the internal components of the surgical tool 400 may be damaged if the joint 1300 is articulated to its limits at elevated speeds. For example, impact resulting from the joint 1300 hitting its limits at high speed may break the drive pins 1060a,b (FIG. 10B) of the articulation member 808 (FIGS. 9A-9B and 10A-10B) and/ or the drive members 720a,b. Thus, systems and methods are disclosed herein for controlling the joint 1300 and preventing it from hitting its physical limits at elevated speeds, and thereby minimizing or avoiding impact on the underlying mechanisms that articulate the joint 1300 and the wrist 406.

Figure 16:
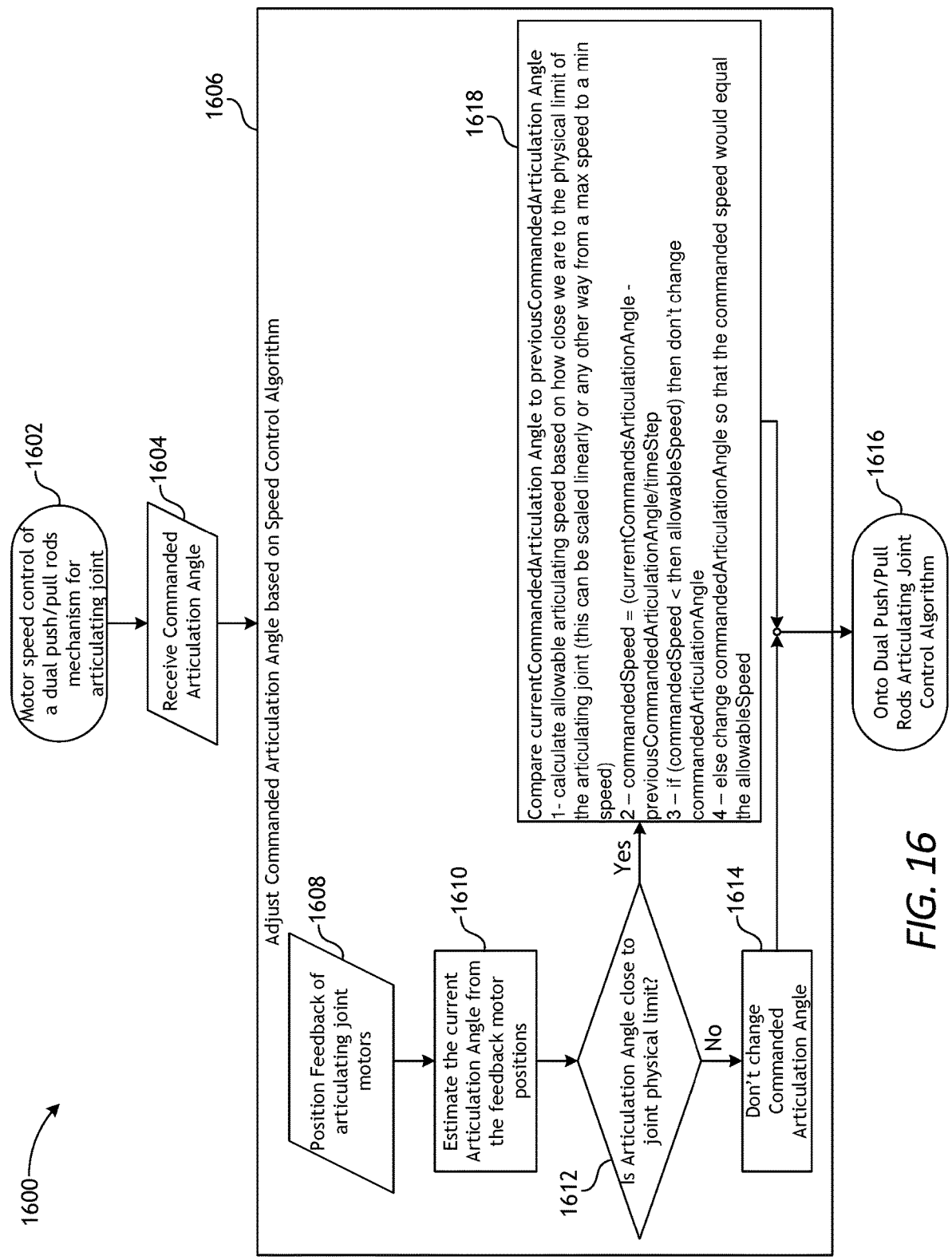
FIG. 16 is a schematic of another exemplary method for controlling articulation of the joint of FIG. 13, according to one or more embodiments of the disclosure.

FIG. 16 is a schematic diagram of an alternate example control method or scheme 1600 for quickly controlling articulation of the wrist 406 while simultaneously preventing the joint 1300 of FIG. 13 to hit its physical limits at high speed, according to one or more embodiments. In the illustrated example, the control scheme 1600 allows the drivers 610b,c that cause translation (motion) of the drive members 720a,b, and thereby articulation of the joint 1300, to move at maximum speed when an instantaneous angle of the joint 1300, which is estimated or measured based on feedback as to the position of the drivers 610b,c, is within defined safe limits. When the instantaneous angle of the joint 1300 is determined to be outside of the defined safe limits, the control scheme 1600 slows the speed of the drivers 610b,c as the joint 1300 articulates at angles approaching the physical limits of the joint 1300.

The joint 1300 has a known range of articulation that defines the amount by which the wrist 406 may angle from its unarticulated position when it extends straight along the longitudinal axis $A_1$ of the shaft 402. For example, the joint 1300 may be configured to articulate clockwise or counter-clockwise sixty degrees (60°) relative to the longitudinal axis $A_1$ (FIG. 4) before hitting its physical limits. Thus, in this example, the range of articulation of the joint 1300 would be plus or minus sixty degrees (±60°) from the longitudinal axis $A_1$, such that the joint 1300 has a physical limit at sixty degrees (60°) in either direction from the longitudinal axis $A_1$, and thereby providing the joint 1300 with a total of one hundred and twenty degrees (120°) of articulation. A safe limit may be defined at any point within the range of articulation. For example, a safe limit may be defined at plus or minus fifty-five degrees (±55°) from the longitudinal axis $A_1$, such that the joint 1300 has a safety limit at fifty-five degrees (55°) in either direction from the longitudinal axis $A_1$, and thereby providing the joint 1300 with a range of one hundred and ten degrees (110°) of articulation between the safety limits.

In this example, the control scheme 1600 operates the drivers 610b,c at a first speed when the joint 1300 is articulated at an instantaneous angle $\angle A$ less than plus or minus fifty-five degrees ($\angle A < \pm 55°$) from the longitudinal axis $A_1$, and then decreases the speed of the drivers 610b,c when the instantaneous angle $\angle A$ of the joint 1300 is greater than or equal to fifty-five degrees ($\angle A \geq \pm 55°$). Thus, the control scheme 1600 slows the drivers 610b,c when the instantaneous angle $\angle A$ of the joint 1300 approaches or is near the physical limits (e.g., $\pm 60° > \angle A \geq \pm 55°$) and speeds up the drivers 610b,c when the instantaneous angle $\angle A$ of the joint 1300 is within the safety limits (e.g., $\angle A$ is between $-55°$ and $55°$).

When the control scheme 1600 determines that the instantaneous angle $\angle A$ of the joint 1300 is beyond the safety limits (e.g., $-60° \leq \angle A \geq -55°$ or $55° \leq \angle A \leq 60°$), the control scheme 1600 slows the drivers 610b,c. In one example, the control scheme 1600 slows the drivers 610b,c to a second speed that is less than the first speed at which the drivers 610b,c operate when the instantaneous angle $\angle A$ of the joint 1300 is within the safety limits. In other examples, however, the control scheme 1600 continuously decreases the speed of the drivers 610b,c as the joint 1300 approaches the physical limits, such that the control method 1600 operates the drivers 610*b,c* at a range decreasing speeds when the instantaneous angle ∠A of the joint 1300 is beyond the safety limits. For example, the control scheme 1600 may slow the drivers 610*b,c* when the instantaneous angle ∠A of the joint 1300 at the safety limit, and then further slow the drivers 610*b,c* as the instantaneous angle ∠A of the joint 1300 further approaches the physical limit.

Thus, after initializing the control scheme 1600, as represented by a starting point 1602 in FIG. 16, the control scheme 1600 is configured to receive a commanded articulation angle indicative of the angle into which the joint 1300 is to be articulated, as at 1604. More specifically, the control scheme 1600 includes an input from the clinician 112*a* that represents the angle into which the clinician 112*a* desires to move the wrist 406. Upon receiving the commanded articulation angle input via the input 1604, the control scheme 1600 initiates a process to adjust the commanded articulation angle based on a speed control algorithm, as at 1606.

Upon initialization of the process, the control scheme 1600 receives feedback 1608 indicative of the position of the drivers 610*b,c*, as at 1608. Then, the control scheme 1600 uses the feedback information to estimate the current angle at which the joint 1300 is articulated, as at 1610. Then, the control scheme 1600 makes a determination as to whether the articulation angle of the joint 1300 is close to a physical limit of the joint 1300, as at 1612. If the articulation angle of the joint 1300 is not close to, or within a range preceding a limit, the control scheme 1600 initiates an instruction to not change the commanded articulation angle (i.e., to maintain commanded articulation angle) of the joint 1300, as at 1614. The control scheme 1600 may end at this point, as represented by a stopping point 1616. Various other systems or control schemes may be initiated after the stopping point 1616. For example, the stopping point 1616 of the control scheme 1600 may correspond with the starting point 1402 of the control scheme 1400 detailed above. Thus, robotic surgical system 100 may be configured to run the control scheme 1600 and the control scheme 1400 in succession.

If the articulation angle of the joint 1300 is close to (or within a range preceding a limit), the control scheme 1600 initiates an instruction causing the joint 1300 to move at a prescribed or allowable speed before reaching the stopping point 1616, as at 1618. Thus, the instruction will cause the drivers 610*b,c* to rapidly move the joint 1300 into the desired articulation angle or to the physical limit of the joint 1300 to the extent that the desired articulation angle is within the permissible range of motion of the joint 1300. In the illustrated example, the instruction at 1618 continuously compares the current commanded articulation angle to the previous commanded articulation angle to determine when motor positions of the drivers 610*b,c* are nearing the physical limits of the joint 1300. The instruction may calculate the allowable speed(s) at which the drivers 610*b,c* operate to articulate the joint 1300 based on how close the joint 1300 is to its physical limits, or based on where the joint 1300 is within a safe zone immediately preceding a physical limit of the joint 1300.

The control scheme 1600 may be configured to vary the speed of the motors 130*a,b* as the joint 1300 articulates between its physical limits based on the proximity of the joint 1300 to its physical limits. For example, the instruction at 1618 may scale the speed of the drivers 610*b,c* (e.g., linearly or non-linearly) from a maximum speed to a minimum speed as the joint 1300 approaches a physical limit. In one example, the instruction commands the drivers 610*b,c* to operate at a command speed equal to the difference between the current commanded articulation angle and the previous commanded articulation angle, divided by the time step between those two measurements (i.e., CommandSpeed=(CurrentCommandedArticulationAngle−PreviousCommandedArticulationAngle)/TimeStep). If the command speed is less than the allowable speed calculated by the control scheme 1600, then the instruction 1618 need not change the commanded articulation angle. But, if the command speed is greater than or equal to the allowable speed calculated by the control scheme 1600, then the instruction 1618 changes the commanded articulation angle so that the command speed would equal the allowable speed.

The robotic surgical system 100 of FIG. 1 may be configured to cause the surgical tool 400 (FIG. 4) to accurately respond as directed by the clinician 112*a* (FIG. 1). However, various conditions may exist (or come into existence during use) that impair or inhibit the surgical tool 400 from accurately responding to input from the clinician 112*a*. For example, accuracy of the surgical tool 400 may be affected by conditions such as mechanical wear, frictional changes, user abuse, service damage, etc., and these conditions may change during use. To ensure operation of the surgical tool 400 correlates to commands input by the clinician 112*a* (i.e., positional accuracy), the robotic surgical system 100 may include a robust error detection system to compensate for various conditions that may change during use of the surgical tool 400. Such error detection systems may be useful for ensuring accuracy of various functions of the surgical tool 400, including homing sequences, articulation of the wrist 406, closure and/or grasping of the jaws 410, 412, etc. Thus, control systems and schemes are disclosed herein for ensuring accuracy of the surgical tool 400 by detecting errors in position of the surgical tool 400 based on positional values recorded on the surgical tool 400 during manufacture.

In some embodiments, the surgical tool 400 may include physical features (or stops) that limit the various motions of the end effector 404 (FIG. 4) and/or the wrist 406 (FIG. 4) to a predefined range of motion. These features may be set or calibrated into the surgical tool 400 during its manufacture to correspond to various movements or positions of the end effector 404 and/or the wrist 406. For example, the features may be set during manufacture to correlate to a fully advanced position of the end effector 404, a fully articulated position of the wrist 406, a home position of the wrist 406, or any other desired position.

As mentioned above, the surgical tool 400 may include an internal computer 622 (FIG. 4) that may include a memory 624 (FIG. 4), and the position at which the physical features are set may be stored in the memory 624 and utilized as a target to determine whether it is operating accurately. For example, the surgical tool 400 may be calibrated during manufacture to determine how many rotations of a given drive input 608*a-f* (FIG. 6) is needed to move the end effector 404 and/or the wrist 406 into a desired position and to determine the specific angle at which the drive inputs 608*a-f* are oriented when in the desired position, and this information may be stored in the memory 624. In addition, each surgical tool 400 may be calibrated during its manufacture to measure the torque assumed on the drive inputs 608*a-f* as they are fully rotated from the home position in each direction, and this torque information may be recorded in the memory 624. Also, where two or more of the drive inputs 608*a-f* are utilized to move the end effector 404 and/or the wrist 406, the relative position of the drive inputs 608*a-f* may be recorded in the memory 624. With any or all of this information stored in the memory, the accuracy control system may provide feed specific to the particular surgical tool 400 that is engaged in the robotic manipulator.

In various examples, the accuracy control system may be utilized for homing one or more of the drive inputs 608a-f (FIG. 6). In examples where two or more of the drive inputs 608a-f are actuated to cause a particular movement of the surgical tool 400 (FIG. 4), the actual angular position of the drive inputs 608a-f when in the home position and the relative position of (i.e., the angular difference between) the drive inputs 608a-f when in the home position are stored in the onboard memory 624 (FIG. 6) of the surgical tool 400 during manufacture. Then, when the surgical tool 400 is installed on the robotic manipulator, the accuracy control system reads the position of one of the drive inputs 608a-f as it rotates in the "home" direction, simultaneously calculating the position of the associated drive input(s) 608a-f via the relative position data stored in the memory 624, until all of the associated drive inputs 608a-f reach, within some error, the position recorded in the memory.

In examples where just one of the drive inputs 608a-f is used to cause a particular movement of the surgical tool 400, the home position of the particular one of the drive inputs 608a-f is stored in the memory 624 (FIG. 6) and the accuracy control system may determine whether the particular drive input 608a-f is in the "home position" as the corresponding driver 610a-f (FIG. 6) rotates it in the "home" direction by comparing the actual angular position the drive input 608a-f to the "home" position stored in the memory when the surgical tool 400 is mounted in the robotic manipulator. In these examples, if the particular driver 610a-f rotates the corresponding drive input 608a-f less than 360°, the accuracy control system may establish the home position of the drive input 608a-f when the surgical tool 400 is installed on the robotic manipulator. In some examples, if the travel of any of the drive inputs 608a-f is greater than 360°, the "home" position recorded in the memory 624 could be utilized as a confirmation check in combination with other homing control schemes as described herein. Thus, the accuracy control system may check whether the drive inputs 608a-f are in their home position(s) based on information stored in the onboard memory 624.

In some examples, the accuracy control system may be expanded to cross-check other non-home positions of the drive inputs 608a-f. For example, the accuracy control system may be utilized for accurately rotating one or more of the drive inputs 608a-f (FIG. 6) to effectuate a desired movement or position of the surgical tool 400 (FIG. 4) by comparing the actual or instantaneous position of the surgical tool 400 achieved during operation to a set value stored in the memory 624 (FIG. 6). In these examples, the surgical tool 400 is calibrated during manufacture, with the position of the end effector 404 (FIG. 4) and/or the wrist 406 (FIG. 4) being correlated with the position of the various drive inputs 608a-f and the torque applied thereto via the corresponding drivers 610a-f (FIG. 6), and such calibration information is stored in the memory 624 of the surgical tool 400. For example, rotational positions and/or torques of any of the drive inputs 608a-f corresponding with a fully advanced position of the end effector 404 (e.g., fully expanded jaws 410, 412), fully angled position of the wrist 406, and/or a home position of the end effector 404 and/or the wrist 406, etc. may be recorded in the memory 624. This stored information provides a target that is specific or unique to the particular surgical tool 400 installed in the robotic manipulator. If the robotic surgical system 100 (FIG. 1) drives one or more of the drivers 610a-f to a particular position and the actually achieved position of the end effector 404 and/or the wrist 406 of the surgical tool 400 does not correlate with the position information stored in the memory 624, the accuracy control system will report an error in position.

In some examples, the accuracy control system is incorporated with two or more of the drive inputs 608a-f (FIG. 6). For example, the accuracy control system may be utilized with the drive inputs 608b,c that control the wrist 406 (FIG. 4) and/or with the drive inputs 608d,e that control the jaws 410, 412 (FIG. 4). In these examples, during manufacture of the surgical tool 400 the absolute angular positions of two or more of the drive inputs 608a-f when the surgical tool 400 is at a set desired position (i.e., the desired position of the end effector 404 and/or the wrist 406) are read and stored in the memory 624 (FIG. 6), and also the relative angular position between the drive inputs 608a-f corresponding with the set position of the surgical tool 400 (i.e., the angular difference between the drive inputs 608a-f) is recorded in the memory 624. The absolute angle of the drive inputs 608a-f corresponds to a globally consistent angle that is consistent over time and over robot-power cycles. For example, a graphical arrow may be provided on the drive input 608a-f such that it may be determined that, when such graphical arrow is aligned with a corresponding graphical arrow on the tool driver 604 of the robot, the angle of the drive input 608a-f is "absolute zero." When the surgical tool 400 is installed in a robotic manipulator and the clinician 112a inputs a command to move the surgical tool 400 to a desired position, if the actual position of the drive inputs 608a-f corresponding with the clinician's 112a desired movement does not match the positional information stored in the memory 624, the accuracy control system would report an error.

In other examples, the accuracy control system is incorporated with just one of the drive inputs 608a-f. In these examples, the absolute position of one of the drive inputs 608a-f corresponding with a set desired position of the surgical tool 400 would be stored in its memory 624 during manufacture or calibration and, during use, the accuracy control system could check whether the surgical tool 400 is in the desired position.

In some examples, the accuracy control system may be configured to detect a closure error of the jaws 410, 412 (FIG. 4) where the actual positions of the drive inputs 608a-f (FIG. 6) corresponding with the jaws 410, 412 being closed do not match the fully-closed positions of the drive inputs 608a-f set during manufacture. In some examples, the accuracy control system may be configured to detect an opening error of the jaws 410, 412 where the actual positions of the drive inputs 608a-f corresponding with the jaws 410, 412 being fully open do not match the fully open positions of the drive inputs 608a-f set during manufacture. In some examples, the accuracy control system may be configured to detect a grasping error of the jaws 410, 412 where the actual positions of the drive inputs 608a-f corresponding with the jaws 410, 412 grasping at a set position relative to each other do not match the grasping positions of the drive inputs 608a-f set during manufacture. In some examples, the accuracy control system may be configured to monitor the change in any of the above positions over use of the surgical tool 400 and, if they change by a specified amount (or more), the accuracy control system may be configured report a wear error.

The robotic surgical system 100 (FIG. 1) may further include or incorporate a control scheme that moves the drive members 720a,b synchronously, meaning that, the second driver 610b (FIG. 6) of the tool driver 604 (FIG. 6) causes translation of the first drive member 720a and the third driver 610c causes an equal and opposite translation of the second drive member 720b. For example, a left-hand articulation of the wrist 406 (FIG. 4) is accomplished by moving the first drive member 720a proximally a distance "x" while moving the second drive member 720b distally a distance "−x". The robotic surgical system 100 commands the drivers 610b,c (that engage the drive inputs 608b,c) to rotate into motor positions necessary to cause translation of the drive members 720a,b distances of "x" and "−x", respectively. Thus, driver position commands R3 and R4 may be calculated to synchronously translate the drive members 720a,b based on an input from the clinician 112a (i.e., articulationAngleCommanded). The driver position commands R3, R4 may be calculated using the following equations:

$$x: R3 = GearRatio * \left(\frac{180}{\pi}\right) * pinRadius * \frac{\sin\left(articulationAngleCommanded * \frac{\pi}{180}\right)}{gearRadius}$$

$$-x: R4 = GearRatio * \left(\frac{180}{\pi}\right) * pinRadius * \frac{\sin\left(articulationAngleCommanded * \frac{\pi}{180}\right)}{gearRadius}$$

This control scheme translates input from the clinician 112a (i.e., articulationAngleCommanded) into rotation of the drivers 610b,c. In this control scheme, the values "x" and "−x" are not directly calculated, as the input from the clinician 112a is the desired angle to move the wrist 406 and, from that input, the control scheme outputs the rotary input or control of the driver 610b,c (i.e., the driver position commands R3, R4). To calculate "x", the formula would be x=R3*GearRatio*2*n*gearRadius, and "−x" may be similarly calculated. The forgoing formulae include mathematical representations of the psychical components of the surgical tool 400, where pinRadius is the distance from the center of the pivot shaft 1034 to the center of the drive pins 1060a,1060b, GearRatio is the ratio created from the spur gear 709a,b through the idler assembly 715a,b (i.e., the compound gear) to the compound pinion gear 710a,b, and gearRadius is the radius of the second pinion gear 713a,b (of the compound pinion gear 710a,b) that interacts with the drive rack 712a,b.

This synchronous control scheme, however, may not accurately articulate the wrist 406 into the desired articulation angle commanded by the clinician 112a. For example, friction resulting from wear may cause the wrist 406 to articulate only 40° degrees despite the clinician 112a having input a desired articulation angle of 45°. In addition to decreasing accuracy of articulation, this synchronous control scheme may incur decreased mechanical advantage as the wrist 406 articulates at increasing angles over time.

Thus, the robotic surgical system 100 may include improved control schemes configured to enhance articulation of the wrist 406. In some examples, the robotic surgical system 100 includes a differential control scheme for controlling movement of the drive members 720a,b to more accurately articulate the wrist 406 into the desired wrist position input by the clinician 112a. In various examples, the differential control scheme may also increase the maximum angles to which the wrist 406 may articulate and increase the mechanical advantage of the wrist 406 (i.e., the force at which it may articulate).

The differential control scheme is a passive control that calculates the driver position commands R3, R4 by which the drive members 720a,b are moved utilizing the formulae described above and modified by a constant α or a mathematical function. For example, the differential control scheme accomplishes a left-hand articulation of the wrist 406 by moving the first drive member 720a a distance "x" via the first motor command R3 while moving the second drive member 720b a distance "−x−α" via the second motor command R4. Thus, one side of the articulation system may move more (or less) than the other side. In this example described, if the geometry were perfect and there were no friction the constant α would increase the tension in the system. If the constant α is a constant then the increase in tension would be applied only when the articulationAngleCammanded is greater (or lesser) than 0. However, the constant α may be described as increasing or decreasing as a function of the articulationAngleCommanded, and, as described below, the constant α may be an empirically determined value and/or based on a mathematical function.

In some examples, the constant α may be empirically determined. In these examples, the constant α may be empirically determined during testing, manufacture, and/or calibration of the surgical tool 400 and, therefore, the constant α may be unique to each surgical tool 400. Here, the constant α may act as a correction factor for the gear/linkage mechanism controlling the wrist 406, between a nominal condition and an actual condition for which friction and wear (e.g., stretch of the drive members 720a,b) is accounted.

In one example, each of the surgical tools 400 during manufacture is placed in a testing apparatus that senses articulation angle of the wrist 406 while rotating the drive inputs 608b,c. The value of the constant α may be adjusted to minimize error between the actual measured articulation angle of the wrist 406 and the expected articulation angle of the wrist 406, and then the value of the constant α may be saved on the memory of the surgical tool 400 to be utilized by the robotic surgical system 100 during an operation. When the actual measured articulation angle of the wrist 406 is minimized, the value of the constant α would be flashed to the surgical tool 400 so that the robotic surgical system 100 may use it.

In other examples, the constant α may be a value that is modified by a function. In these examples, the constant α may be assigned a value or a value may be empirically determined as described above. Regardless, the constant α may be modified by various functions of the desired angle input by the clinician 112a (i.e., articulationAngleCommanded), such as linear functions, sinusoidal functions, exponential functions, polynomial functions, or any combination thereof. Thus, driver position commands R3, R4 are calculated to translate the drive members 720a,b a distance (i.e., "x" or "−x") based on input from the clinician 112a (i.e., articulationAngleCommanded) minus a correction factor, where the correction factor deducted from the distance is a function of the articulationAngleCommanded multiplied by the constant α.

In one example, the correction factor is a sinusoidal function modifying the constant α. Here, the constant α is a value multiplied by the sin of the desired angle input by the clinician 112a (i.e., articulationAngleCommanded), such that the driver position commands R3, R4 are calculated with the following equations.

If articulationAngleCommanded is >0:

$$R3 = GearRatio * \left(\frac{180}{\pi}\right) * pinRadius * \frac{\sin\left(articulationAngleCommanded * \frac{\pi}{180}\right)}{gearRadius} - \alpha * \sin\left(articulationAngleCommanded * \frac{\pi}{180}\right)$$

$$R4 = GearRatio * \left(\frac{180}{\pi}\right) * pinRadius * \frac{\sin\left(articulationAngleCommanded * \frac{\pi}{180}\right)}{gearRadius}$$

If articulationAngleCommanded is < 0:

$$R3 = GearRatio * \left(\frac{180}{\pi}\right) * pinRadius * \frac{\sin\left(articulationAngleCommanded * \frac{\pi}{180}\right)}{gearRadius}$$

$$R4 = GearRatio * \left(\frac{180}{\pi}\right) * pinRadius * \frac{\sin\left(articulationAngleCommanded * \frac{\pi}{180}\right)}{gearRadius} - \alpha * \sin\left(articulationAngleCommanded * \frac{\pi}{180}\right)$$

In another example, the correction factor is a linear function of the constant α. Here, the constant α is a value multiplied by a linear factor m (i.e., the slope) multiplied by the desired angle input by the clinician 112a (i.e., articulationAngleCommanded) plus b (i.e., the intercept), such that the driver position commands R3, R4 are calculated with the following equations.

If articulationAngleCommanded is >0:

$$R3 = GearRatio * \left(\frac{180}{\pi}\right) * pinRadius * \frac{\sin\left(articulationAngleCommanded * \frac{\pi}{180}\right)}{gearRadius} - \alpha * \left(m\left(articulationAngleCommanded * \frac{\pi}{180}\right) + b\right)$$

$$R4 = GearRatio * \left(\frac{180}{\pi}\right) * pinRadius * \frac{\sin\left(articulationAngleCommanded * \frac{\pi}{180}\right)}{gearRadius}$$

If articulationAngleCommanded is < 0:

$$R3 = GearRatio * \left(\frac{180}{\pi}\right) * pinRadius * \frac{\sin\left(articulationAngleCommanded * \frac{\pi}{180}\right)}{gearRadius}$$

$$R4 = GearRatio * \left(\frac{180}{\pi}\right) * pinRadius * \frac{\sin\left(articulationAngleCommanded * \frac{\pi}{180}\right)}{gearRadius} - \alpha * \left(m\left(articulationAngleCommanded * \frac{\pi}{180}\right) + b\right)$$

In other examples, the correction factor is a polynomial function of the constant α. For example, a polynomial function (where a, b, and c are constants) could be as follows.

If articulationAngleCommanded is >0:

$$R4 = GearRatio * \left(\frac{180}{\pi}\right) * pinRadius * \frac{\sin\left(articulationAngleCommanded * \frac{\pi}{180}\right)}{gearRadius} - \alpha * \left(a * \left(articulationAngleCommanded * \frac{\pi}{180}\right)^2 + b * \left(articulationAngleCommanded * \frac{\pi}{180}\right) + c\right)$$

$$R4 = GearRatio * \left(\frac{180}{\pi}\right) * pinRadius * \frac{\sin\left(articulationAngleCommanded * \frac{\pi}{180}\right)}{gearRadius}$$

If articulationAngleCommanded is <0:

$$R3 = GearRatio * \left(\frac{180}{\pi}\right) * pinRadius * \frac{\sin\left(articulationAngleCommanded * \frac{\pi}{180}\right)}{gearRadius}$$

$$R4 = GearRatio * \left(\frac{180}{\pi}\right) * pinRadius * \frac{\sin\left(articulationAngleCommanded * \frac{\pi}{180}\right)}{gearRadius} - \alpha * \left(a * \left(articulationAngleCommanded * \frac{\pi}{180}\right)^2 + b * \left(articulationAngleCommanded * \frac{\pi}{180}\right) + c\right)$$

In other examples, the correction factor is an exponential function of the constant α. For example, an exponential function (where e is a constant) could be as follows.

If articulationAngleCommanded is >0:

$$R3 = GearRatio * \left(\frac{180}{\pi}\right) * pinRadius * \frac{\sin\left(articulationAngleCommanded * \frac{\pi}{180}\right)}{gearRadius} - \alpha * e^{\left(articulationAngleCommanded * \frac{\pi}{180}\right)}$$

$$R4 = GearRatio * \left(\frac{180}{\pi}\right) * pinRadius *$$

-continued $$\frac{\sin\left(articulationAngleCommanded * \frac{\pi}{180}\right)}{gearRadius}$$

If articulationAngleCommanded is <0:

$$R3 = GearRatio * \left(\frac{180}{\pi}\right) * pinRadius * $$

$$\frac{\sin\left(articulationAngleCommanded * \frac{\pi}{180}\right)}{gearRadius}$$

$$R4 = GearRatio * \left(\frac{180}{\pi}\right) * pinRadius * $$

$$\frac{\sin\left(articulationAngleCommanded * \frac{\pi}{180}\right)}{gearRadius} - $$

$$\alpha * e^{\left(articulationAngleCommanded * \frac{\pi}{180}\right)}$$

Figure 17B:
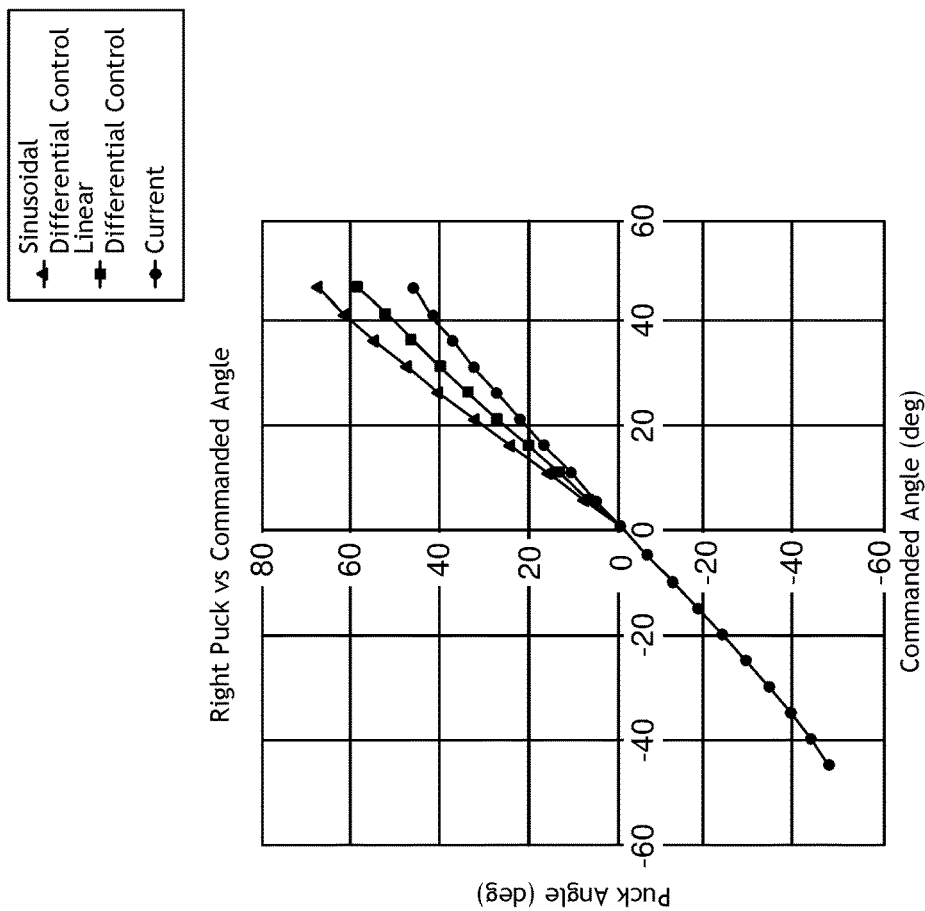
FIGS. 17A and 17B are plots illustrating an exemplary differential control for actuating the wrist, according to one or more embodiments of the disclosure.
Figure 17A:
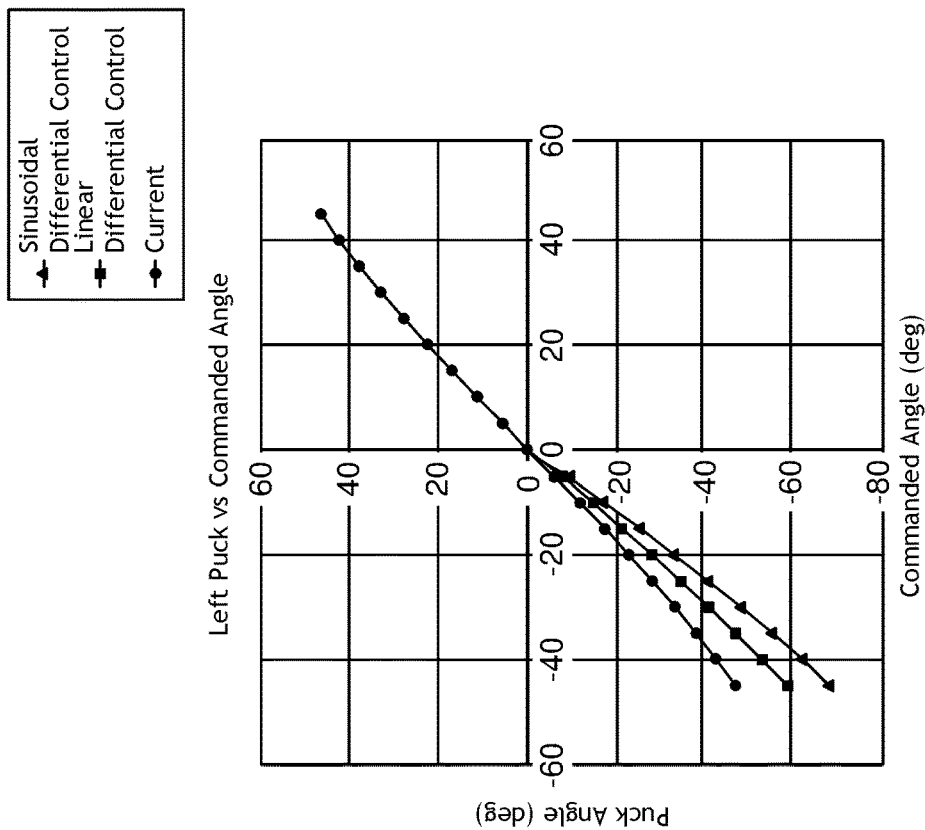

FIGS. 17A and 17B are graphical representations illustrating the actual angular position output versus the desired angular input for each of the drive inputs 608b,c (FIG. 6) utilizing the foregoing equations, according to one or more embodiments. In particular, FIG. 17A plots the actual angular position obtained for the second drive input 608b for each desired angular position input by the clinician 112a (i.e., articulationAngleCommanded) under the current control scheme, the sinusoidal control scheme, and the linear control scheme. Similarly, FIG. 17B plots the actual angular position obtained for the third drive input 608c for each desired angular position input by the clinician 112a (i.e., articulationAngleCommanded) under the current control scheme, the sinusoidal control scheme, and the linear control scheme. Thus, as the end effector 404 moves to the right (from center) the angular displacement of the right drive input increases at a greater rate than the left drive input, and when the end effector 404 moves to the left (from center) the angular displacement of the left drive input increases at a greater rate than the right drive input.

The surgical tool 400 (FIG. 4) described and illustrated herein is configured as a "rotary surgical tool" because it includes rotary drive inputs 608a-f (FIG. 6) that are each rotated by a corresponding driver 610a-f (FIG. 6) on the robotic manipulator. In other examples, however, the surgical tool 400 may be differently configured such that it may be actuated by drivers configured to impart different types of mechanical energy. For example, the surgical tool 400 may be configured as a linear drive tool having one or more linear drive inputs as described in U.S. Patent Application Publication No. 2018/0168745, the contents of which are hereby incorporated by reference. In some examples, the surgical tool 400 may include a combination of both rotary and linear drive inputs.

In some embodiments, the robotic surgical system 100 (FIG. 1) may include a closure control system configured to optimize the closure stroke of the closure tube 722 (FIGS. 7A-7B and 8A-8B). The closure control system may monitor the stroke distance and the force applied to the closure tube 722 during closure of the jaws 410, 412 to determine the inflection point at which the closure tube 722 has translated too far (i.e., over travel) along longitudinal axis $A_1$ (FIGS. 4, 6, and 7A-7B). Thus, the closure control system may limit actuation of the drive inputs (e.g., the fourth and fifth drive inputs 608d,e of FIG. 6) to translate the closure tube 722 the minimum stroke distance required to close the jaws 410, 412 in a particular application. The closure control system may thereby increase reliability of the surgical tool 400 by limiting application of high forces as needed. For example, increased force will typically be applied to the closure tube 722 when manipulating thicker tissue; whereas, lesser amounts of force will be applied when manipulating tissue having less thickness. In addition, the closure tube 722 will not be subjected to an over-closure event during closure of the jaws 410, 412. Moreover, the closure control system reduces the maximum closure stroke of the closure tube 722 as the mechanism is less sensitive to mechanical variation and/or tolerance. Thus, instead of the mechanism translating the closure tube 722 to the maximum possible needed (depending on tissue variation and/or mechanical variation), the mechanism need only translate the closure tube 722 a sufficient amount to achieve an inflection point.

Figure 18:
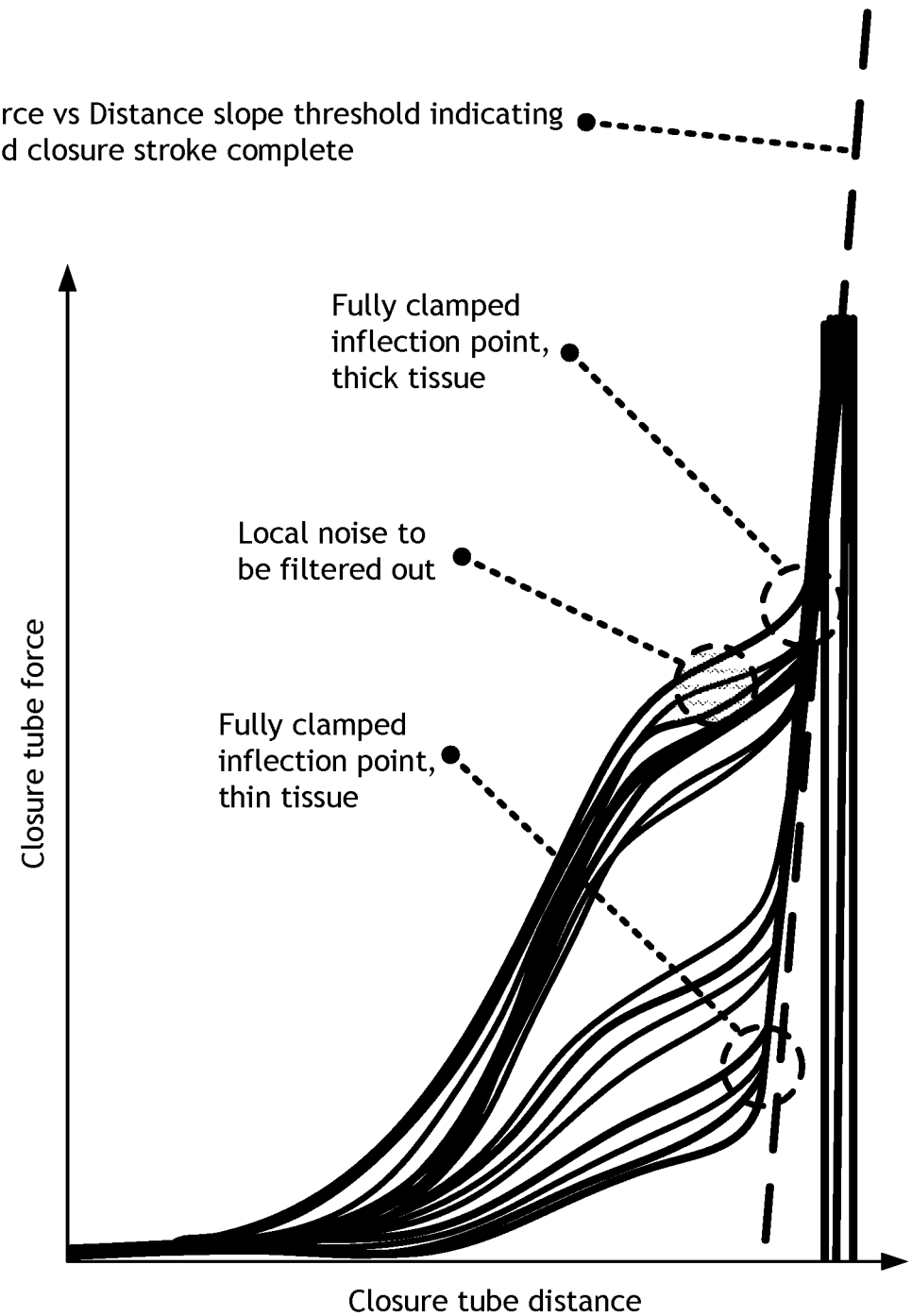
FIG. 18 illustrates a force versus distance curve of an exemplary closure system, according to one or more embodiments of the disclosure.

FIG. 18 illustrates a force-distance graph of an exemplary closure control system, according to one or more embodiments. In this example, the closure control system is configured to extend the closure tube 722 (FIGS. 7A-7B and 8A-8B) by actuating the corresponding drivers (e.g., the fourth and fifth driver 610d,e of FIG. 6) corresponding with the appropriate drive inputs (e.g., the fourth and fifth drivers inputs 608d,e of FIG. 6). The current required to drive the drivers is recorded and equated to a force utilizing constants stored in the memory 624 (FIG. 6) of the surgical tool 400. Also, the angular position of the drivers is recorded and equated to a travel amount via mechanism dependent constants stored in the memory 624. As the closure tube 722 is being closed, the closure control system calculates the derivative of force versus distance and utilizes a low-pass filter to remove spikes in the curve that are caused by noise. Then, when the filtered force versus distance derivative exceeds a mechanism-dependent threshold stored in the memory of the surgical tool 400, the closure control system will stop further travel of the closure tube 722 and/or other closure mechanisms, and report that the surgical tool 400 is fully clamped. Upon receiving a report that the surgical tool 400 is fully clamped, the robotic surgical system 100 (FIG. 1) may direct the surgical tool 400 to fire and thereby transect and apply staples to the tissue clamped therein.

Embodiments disclosed herein include:

A. A surgical tool includes a drive housing, a shaft that extends from the drive housing, a wrist arranged at an end of the shaft, and a linkage assembly actuatable to articulate the wrist in a plane and including a first drive member extending within the shaft from the drive housing and being operatively connected to the wrist, and a second drive member extending within the shaft from the drive housing and being operatively connected to the wrist. Wherein actuation of the first and second drive members in opposite axial directions within the shaft causes the wrist to articulate in the plane.

B. A method of homing a rotatable drive input of a robotic surgical tool includes recording a home position of the drive input in a memory of the robotic surgical tool, establishing a slow zone encompassing a known angular magnitude away from the home position, and rotating the drive input toward the home position, and slowing a rotation speed of the drive input upon reaching the slow zone.

C. A system for controlling articulation of a joint in a surgical tool driven by a robotic manipulator, the surgical tool having first and second drive members operatively coupled to the joint and arranged to translate in opposite directions when actuated by respective first and second drivers of the robotic manipulator, wherein, upon receiving a command to rotate the joint in a first rotational direction, the first driver actuates and thereby pushes the first drive member distally and, simultaneously, the second driver actuates and thereby pulls the second drive member proximally, thereby rotating the joint in the first rotational direction, wherein, upon receiving a command to rotate the joint in a second rotational direction opposite the first rotational direction, the second driver actuates and thereby pushes the second drive member distally and, simultaneously, the first driver actuates and thereby pulls the first drive member proximally, thereby rotating the joint in the second rotational direction.

D. A system for controlling antagonistic translation of a pair of drive members in a surgical tool, the surgical tool being mountable to a robotic manipulator having a first driver operable to translate the first drive member and a second driver operable to translate the second drive member, wherein, upon receiving a desired articulation angle input, the system determines a first driver position command and a second driver position command at which the first and second drivers will cause translation of the first and second drive members, respectively, to achieve the desired articulation angle input, wherein the first driver command causes the first drive member to translate a distance in a proximal direction and the second driver command causes the second drive member to translate the distance in a distal direction, and wherein the distance is modified by a correction factor.

Each of embodiments A, B, C, and D may have one or more of the following additional elements in any combination: Element 1: wherein the wrist includes a base and an articulation member that is rotatable relative to the base when acted upon by the first and second drive members. Element 2: wherein the base includes a pivot shaft that is disposed within an aperture of the articulation member, the pivot shaft defining an articulation axis about which the articulation member rotates. Element 3: wherein the first drive member is coupled to a first drive pin of the articulation member and the second drive member is coupled to a second drive pin of the articulation member. Element 4: wherein the linkage assembly further includes a distal link that couples distal ends of the first and second drive members at the wrist. Element 5: wherein the first drive pin of the articulation member is disposed within a first aperture of the distal link and the second drive pin of the articulation member is disposed within a second aperture of the distal link. Element 6: wherein the base is connected to an inner grounding shaft that extends proximally within the shaft. Element 7: wherein the first and second drive members are arranged within a first and second slot, respectively, defined within the inner grounding member. Element 8: wherein at least a portion of the first and second slots are defined between an upper surface of the inner grounding member and a lower surface of the base. Element 9: further comprising a first drive shaft rotatably mounted within the drive housing and operatively coupled to the first drive member such that rotation of the first drive shaft causes axial movement of the first drive member, and a second drive shaft rotatably mounted within the drive housing and operatively coupled to the second drive member such that rotation of the second drive shaft causes axial movement of the second drive member. Element 10: wherein the first drive shaft is operatively coupled to the first drive member via a first gear arrangement having a gear ratio greater than or less than 1:1, and the second drive shaft is operatively coupled to the second drive member via a second gear arrangement having a gear ratio greater than or less than 1:1. Element 11: further comprising a first articulation yoke arranged around the inner grounding shaft and operatively coupled to a proximal end of the first drive member and a second articulation yoke arranged around the inner grounding shaft and operatively coupled to a proximal end of the second drive member, wherein axial translation of the first and second articulation yokes causes axial translation of the first and second drive members, respectively. Element 12: wherein the first and second articulation yokes are arranged around the inner grounding shaft such that they rotate with the inner grounding shaft. Element 13: wherein the first drive shaft is operatively coupled to the first drive member via a first drive rack having a first yoke engageable with a first articulation yoke operatively coupled to a proximal end of the first drive member, and wherein the second drive shaft is operatively coupled to the second drive member via a second drive rack having a second yoke engageable with a second articulation yoke operatively coupled to a proximal end of the second drive member.

Element 14: further comprising measuring a rotational position of the drive input with a rotary encoder. Element 15: further comprising detecting a torque spike with one or more torque sensors when the drive input reaches the home position.

Element 16: wherein the first and second drivers of the robotic manipulator maintain equal tension or compression in the first and second drive members until commanded to rotate the joint in either the first or second rotational direction. Element 17: wherein the tension or compression applied by the first and second motors is dependent upon an articulation angle of the joint.

Element 18: wherein the correction factor is an empirically determined constant of the surgical tool. Element 19: wherein the correction factor is a product of a constant and a function, and wherein the function is selected from the group consisting of a linear function, a sinusoidal function, an exponential function, a polynomial function, and any combination thereof.

By way of non-limiting example, exemplary combinations applicable to A, B, C, and D include: Element 1 with Element 2; Element 1 with Element 3; Element 3 with Element 4; Element 4 with Element 5; Element 1 with Element 6; Element 6 with Element 7; Element 7 with Element 8; Element 9 with Element 10; Element 7 with Element 11; Element 11 with Element 12; Element 10 with Element 13; and Element 16 with Element 17.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
    a drive housing;
    a shaft that extends from the drive housing;
    a wrist arranged at an end of the shaft and including:
        a base defining an extension member extending distally from the base, and a pivot shaft defined by the base and extending from the extension member and along an articulation axis; and
        an articulation member defining an aperture that receives the pivot shaft, the articulation member being rotatable about the articulation axis; and
    a linkage assembly actuatable to articulate the wrist in a plane and including:
        a first drive member extending within the shaft from the drive housing and being operatively connected to the wrist at a first drive pin of the articulation member; and
        a second drive member extending within the shaft from the drive housing and being operatively connected to the wrist at a second drive pin of the articulation member,
    wherein actuation of the first and second drive members in opposite axial directions within the shaft causes the articulation member to rotate about the articulation axis and thereby articulate the wrist in the plane.

2. The surgical tool of claim 1, wherein the linkage assembly further includes a distal link that couples distal ends of the first and second drive members at the wrist.

3. The surgical tool of claim 2, wherein the first drive pin of the articulation member is disposed within a first aperture of the distal link and the second drive pin of the articulation member is disposed within a second aperture of the distal link.

4. The surgical tool of claim 2, wherein the distal link defines an interior pivot surface engageable with the base, and the distal link pivots against the interior pivot surface as the articulation member rotates about the articulation axis.

5. The surgical tool of claim 1, wherein the base is connected to a distal end of an inner grounding shaft extending within the shaft.

6. The surgical tool of claim 5, wherein the first and second drive members are arranged within first and second slots, respectively, defined on opposing sides of the inner grounding shaft.

7. The surgical tool of claim 6, wherein at least a portion of the first and second slots are defined between an upper surface of the inner grounding shaft and a lower surface of the base.

8. The surgical tool of claim 5, further comprising a first articulation yoke arranged around the inner grounding shaft and operatively coupled to a proximal end of the first drive member and a second articulation yoke arranged around the inner grounding shaft and operatively coupled to a proximal end of the second drive member, wherein axial translation of the first and second articulation yokes causes axial translation of the first and second drive members, respectively.

9. The surgical tool of claim 8, wherein the first and second articulation yokes are arranged around the inner grounding shaft such that they rotate with the inner grounding shaft.

10. The surgical tool of claim 1, further comprising:
    a first drive shaft rotatably mounted within the drive housing and operatively coupled to the first drive member such that rotation of the first drive shaft causes axial movement of the first drive member; and
    a second drive shaft rotatably mounted within the drive housing and operatively coupled to the second drive member such that rotation of the second drive shaft causes axial movement of the second drive member.

11. The surgical tool of claim 10, wherein the first drive shaft is operatively coupled to the first drive member via a first gear arrangement having a gear ratio greater than or less than 1:1, and the second drive shaft is operatively coupled to the second drive member via a second gear arrangement having a gear ratio greater than or less than 1:1.

12. The surgical tool of claim 10, wherein the first drive shaft is operatively coupled to the first drive member via a first drive rack having a first yoke engageable with a first articulation yoke operatively coupled to a proximal end of the first drive member, and wherein the second drive shaft is operatively coupled to the second drive member via a second drive rack having a second yoke engageable with a second articulation yoke operatively coupled to a proximal end of the second drive member.

13. The surgical tool of claim 1, wherein the first drive member defines a first drive pin aperture that receives the first drive pin, and the second drive member defines a second drive pin aperture that receives the second drive pin, and wherein the first and second drive pin apertures are sized such that the first and second drive pins laterally translate within the first and second drive pin apertures during actuation of the first and second drive members.

14. The surgical tool of claim 1, wherein the articulation axis extends through and is perpendicular to the longitudinal axis.

15. The surgical tool of claim 1, wherein the articulation member provides an annular body that defines the aperture, and the first and second drive pins extend from the annular body on the angularly opposite sides of the aperture.

16. A surgical tool, comprising:

a drive housing;

a shaft that extends from the drive housing along a longitudinal axis;

a wrist arranged at an end of the shaft and including:
- a base providing a pivot shaft that extends along an articulation axis;
- an articulation member defining an aperture that receives the pivot shaft, the articulation member being rotatable about the articulation axis; and a linkage assembly actuatable to articulate the wrist in a plane and including:
- a first drive member extending within the shaft from the drive housing and being operatively connected to the wrist at a first drive pin of the articulation member; and
- a second drive member extending within the shaft from the drive housing and being operatively connected to the wrist at a second drive pin of the articulation member, wherein a curved proximal face of the articulation member slidably engages a curved distal face of the base during operation, and wherein actuation of the first and second drive members in opposite axial directions within the shaft causes the articulation member to rotate about the articulation axis and thereby articulate the wrist in the plane.

17. A surgical tool, comprising:

a drive housing;

a shaft that extends from the drive housing along a longitudinal axis;

a wrist arranged at an end of the shaft and including:
- a base providing a pivot shaft that extends along an articulation axis; and
- an articulation member defining an aperture that receives the pivot shaft, the articulation member being rotatable about the articulation axis; and a linkage assembly actuatable to articulate the wrist in a plane and including:
- a first drive member extending within the shaft from the drive housing and being operatively connected to the wrist at a first drive pin of the articulation member; and
- a second drive member extending within the shaft from the drive housing and being operatively connected to the wrist at a second drive pin of the articulation member, wherein the first and second drive pins are longitudinally aligned with and defined on angularly opposite sides of the aperture, and wherein actuation of the first and second drive members in opposite axial directions within the shaft causes the articulation member to rotate about the articulation axis and thereby articulate the wrist in the plane.

* * * * *